(12) United States Patent
Figueredo et al.

(10) Patent No.: US 8,004,572 B2
(45) Date of Patent: Aug. 23, 2011

(54) SYSTEM FOR TRANSMITTING A VIDEO STREAM OVER A COMPUTER NETWORK TO A REMOTE RECEIVER

(75) Inventors: Vincent Michael Figueredo, Cedar Crest, NM (US); Kendyl Allen Roman, Sunnyvale, CA (US); Paul Raposo, Oakland, CA (US); Richard Scott Neale, Sunnyvale, CA (US); Cyrus J. Hoomani, San Francisco, CA (US); Thomas Joseph Broadbent, Glendora, CA (US)

(73) Assignee: Zin Stai Pte. In, LLC, Dover, DE (US)

( * ) Notice: Subject to any disclaimer, the term of this patent is extended or adjusted under 35 U.S.C. 154(b) by 1296 days.

(21) Appl. No.: 11/633,967

(22) Filed: Dec. 4, 2006

(65) Prior Publication Data

US 2007/0223574 A1    Sep. 27, 2007

Related U.S. Application Data

(62) Division of application No. 09/312,922, filed on May 17, 1999, now Pat. No. 7,257,158.

(51) Int. Cl.
*H04N 9/04* (2006.01)
*A61B 7/04* (2006.01)

(52) U.S. Cl. ...................................... 348/211.8; 381/67
(58) Field of Classification Search ............... 348/211.8, 348/14.13, 14.09, 333.02; 381/67
See application file for complete search history.

(56) References Cited

U.S. PATENT DOCUMENTS 4,301,469 A    11/1981 Modeen et al.
(Continued)

FOREIGN PATENT DOCUMENTS

WO    9959472    11/1999

OTHER PUBLICATIONS

Office Action dated Dec. 17, 2002 for U.S. Appl. No. 09/312,922.
(Continued)

*Primary Examiner* — Gims S Philippe
(74) *Attorney, Agent, or Firm* — Schwabe, Williamson & Wyatt, P.C.

(57) ABSTRACT

A method of and system for transmitting video images preferably allows a specially trained individual to remotely supervise, instruct, and observe administration of medical tests conducted at remote locations. This system preferably includes a source device, a transmitting device, and at least one remote receiving device. The transmitting device, and the remote receiving device communicate over a network such as any appropriate data network. The transmitting device transmits the video images to the remote receiving device either for live display from the source device or for pre-recorded display from a video recorder device. The remote receiving device is also capable of communicating with the transmitting device while simultaneously receiving video images to provide remote control. The source device is preferably a medical test device such as an ultrasound, a sonogram, an echocardiogram, an angioplastigram, and the like. The transmitting device captures the video images in real-time from the source device and compresses these video images utilizing a compression method prior to transmitting data representing the video images to the remote receiving device. The compressor and compression method preferably utilize data structures comprising line number data structures and the repeat data structures. Remote users utilizing the remote receiving devices are capable of viewing a live stream of video and remotely controlling a number of parameters relating to the source device and the transmitting device. Such parameters include compression method, image quality, storage of the video images on the transmitting device, manipulating and controlling the source device, and the like.

22 Claims, 14 Drawing Sheets

U.S. PATENT DOCUMENTS

| | | | |
|---|---|---|---|
| 4,302,775 A | 11/1981 | Widergren et al. | |
| 4,385,363 A | 5/1983 | Widergren et al. | |
| 4,394,774 A | 7/1983 | Widergren et al. | |
| 4,410,916 A | 10/1983 | Pratt et al. | |
| 4,546,385 A | 10/1985 | Anastassiou | |
| 4,550,437 A | 10/1985 | Kobayashi et al. | |
| 4,646,356 A | 2/1987 | Anderson et al. | |
| 4,698,672 A | 10/1987 | Chen et al. | |
| 4,704,628 A | 11/1987 | Chen et al. | |
| 4,743,959 A | 5/1988 | Frederiksen | |
| 5,014,710 A | 5/1991 | Maslak et al. | |
| 5,046,027 A | 9/1991 | Taaffe et al. | |
| 5,047,853 A | 9/1991 | Hoffert et al. | |
| 5,271,072 A | 12/1993 | Yoshida et al. | |
| 5,287,452 A | 2/1994 | Newman | |
| 5,309,232 A | 5/1994 | Hartung et al. | |
| 5,398,062 A * | 3/1995 | Hashimoto et al. | 348/333.02 |
| 5,416,602 A | 5/1995 | Inga et al. | |
| 5,471,989 A | 12/1995 | Roundhill et al. | |
| 5,552,832 A | 9/1996 | Astle | |
| 5,581,613 A | 12/1996 | Nagashima et al. | |
| 5,583,561 A | 12/1996 | Baker et al. | |
| 5,585,839 A * | 12/1996 | Ishida et al. | 348/14.09 |
| 5,619,995 A | 4/1997 | Lobodzinski | |
| 5,621,660 A | 4/1997 | Chaddha et al. | |
| 5,646,618 A | 7/1997 | Walsh | |
| 5,715,823 A | 2/1998 | Wood et al. | |
| 5,721,815 A | 2/1998 | Ottesen et al. | |
| 5,754,820 A | 5/1998 | Yamagami | |
| 5,793,416 A * | 8/1998 | Rostoker et al. | 348/14.13 |
| 5,812,119 A | 9/1998 | Tateyama | |
| 5,812,788 A | 9/1998 | Agarwal | |
| 5,882,206 A | 3/1999 | Gillio | |
| 5,897,498 A | 4/1999 | Canfield, II et al. | |
| 5,920,317 A | 7/1999 | McDonald | |
| 5,959,639 A | 9/1999 | Wada | |
| 5,999,655 A | 12/1999 | Kalker et al. | |
| 6,005,979 A | 12/1999 | Chang et al. | |
| 6,009,346 A | 12/1999 | Ostrow | |
| 6,018,713 A | 1/2000 | Coli et al. | |
| 6,025,854 A | 2/2000 | Hinz et al. | |
| 6,054,990 A | 4/2000 | Tran | |
| 6,058,215 A | 5/2000 | Schwartz et al. | |
| 6,063,032 A | 5/2000 | Grunwald | |
| 6,064,324 A | 5/2000 | Shimizu et al. | |
| 6,078,691 A | 6/2000 | Luttmer | |
| 6,091,777 A | 7/2000 | Guetz et al. | |
| 6,115,485 A | 9/2000 | Dumoulin et al. | |
| 6,144,392 A | 11/2000 | Rogers | |
| 6,181,711 B1 | 1/2001 | Zhang et al. | |
| 6,219,358 B1 | 4/2001 | Pinder et al. | |
| 6,324,599 B1 | 11/2001 | Zhou et al. | |
| 6,335,990 B1 | 1/2002 | Chen et al. | |
| 6,338,119 B1 | 1/2002 | Anderson et al. | |
| 6,339,616 B1 | 1/2002 | Kovalev | |
| 6,384,862 B1 | 5/2002 | Brusewitz et al. | |
| 6,571,392 B1 | 5/2003 | Zigmond et al. | |
| 6,592,629 B1 | 7/2003 | Cullen et al. | |
| 6,651,113 B1 | 11/2003 | Grimsrud | |
| 7,116,357 B1 * | 10/2006 | Oya et al. | 348/211.8 |
| 7,257,158 B1 | 8/2007 | Figueredo et al. | |
| 2001/0021260 A1 | 9/2001 | Chung | |
| 2008/0298603 A1 * | 12/2008 | Smith | 381/67 |

OTHER PUBLICATIONS

Office Action dated Feb. 19, 2003 for U.S. Appl. No. 09/312,922.
Office Action dated Dec. 17, 2003 for U.S. Appl. No. 09/312,922.
Office Action dated Aug. 11, 2004 for U.S. Appl. No. 09/312,922.
Office Action dated May 2, 2005 for U.S. Appl. No. 09/312,922.
Office Action dated Jan. 9, 2006 for U.S. Appl. No. 09/312,922.
Notice of Allowance dated Sep. 21, 2006 for U.S. Appl. No. 09/312,922.
International Search Report dated Nov. 25, 1999 for Application PCT/US99/10894.
Adelson, Joshua; Streaming Video on the Net Gains Speed; Electronic Engineering Times; Nov. 17, 1997.
Schneider, Polly, A Faster, Multimedia Internet?; Healthcare Informatics, Online; Jun. 1998.
Live Transmission of Ultrasound Exam; PR Newswire; Nov. 30, 1998.
Gillespie, Greg; Providers Show Some Backbone; Healthcare Data Management; Mar. 1, 2000.
IntraCon Corporation company Interview: James Nation; The Wall Street Transcript; Mar. 6, 2000.
Heart to Heart completes 17th Humanitarian Aid Mission to St. Petersburg Russia; Heart to Heart, a biannual publication of Heart to Heart Children's Medical Alliance; Winter 1999, vol. 1 Issue 3.
IntraCon announces ultrasound transmission technology; Product news, radiologybiz.com; Feb. 17, 2000.
Ultrasound on the Internet?; Health Industry Distributors Association; www.hida.org/govtrelations/updates; Feb. 28, 2000.
Cohen, Jason Z.; Intranet Ultrasound Technology Expected; Los Angeles Daily News; Feb. 17, 2000.
Robertson, Kathy; Software sends ultrasound images over the internet; Sacramento Business Journal Feb. 25, 2000.
Robertson, Kathy; Software will send ultrasound images over the Internet; The Business Journal Serving San Jose and Silicon Valley; Mar. 10, 2000.
Intracom offers Doctors Ultrasound on the Internet; Feb. 17, 2000.
Kincade, Kathy, Software package makes Intranet-based real-time ultrasound a reality; Diagnostic Imaging Online, Miller Freeman, Inc.; www.dimag.com/db_area/archivesonline/2000; Mar. 2000.
FDA grants clearance to Internet ultrasound system, PACS Networking News, Mar. 2000.
Netherby, Jennifer; System Lets Doctors Make Diagnosis via the Internet; San Fernando Valley Business Journal; Mar. 20, 2000.
Manos, Diana; Ultrasound software hits the Internet; Hospitals & Health Networks, American Hospital Publishing, Inc.; May 1, 2000, vol. 74, No. 5.
eHealth Information on the Internet, Market and Corporate Developments; Medical & Healthcare Market Guide, Jan. 21, 2000.
Statement of Vice Admiral Harold Koenig, Medical Corps, U.S. Navy, surgeon General of the Navy, before the Senate Appropriations Committee on Defense; The United States Navy on the World Wide Web, www.navy.mil; Apr. 1, 1998.

* cited by examiner

```
unsigned char encodePalette[ ] = {

| Line Number | A | B | C | D | E | F | G | H | I | J |
|---|---|---|---|---|---|---|---|---|---|---|
| 0 | 0 | 1 | 2 | 3 | 4 | | | | | 0 |
| 1 | 5 | 6 | 7 | 8 | 9 | 10 | 11 | 12 | | 8 |
| 2 | 13 | 14 | 15 | 16 | 17 | 18 | 19 | 20 | | 16 |
| 3 | 21 | 22 | 23 | 24 | 25 | 26 | 27 | 28 | 29 | 24 |
| 4 | 30 | 31 | 32 | 33 | 34 | 35 | 36 | 37 | | 33 |
| 5 | 38 | 39 | 40 | 41 | 42 | 43 | 44 | 45 | | 41 |
| 6 | 46 | 47 | 48 | 49 | 50 | 51 | 52 | 53 | | 49 |
| 7 | 54 | 55 | 56 | 57 | 58 | 59 | 60 | 61 | 62 | 57 |
| 8 | 63 | 64 | 65 | 66 | 67 | 68 | 69 | 70 | | 66 |
| 9 | 71 | 72 | 73 | 74 | 75 | 76 | 77 | 78 | | 74 |
| 10 | 79 | 80 | 81 | 82 | 83 | 84 | 85 | 86 | | 82 |
| 11 | 87 | 88 | 89 | 90 | 91 | 92 | 93 | 94 | 95 | 90 |
| 12 | 96 | 97 | 98 | 99 | 100 | 101 | 102 | 103 | | 99 |
| 13 | 104 | 105 | 106 | 107 | 108 | 109 | 110 | 111 | | 107 |
| 14 | 112 | 113 | 114 | 115 | 116 | 117 | 118 | 119 | | 115 |
| 15 | 120 | 121 | 122 | 123 | 124 | 125 | 126 | 127 | 128 | 123 |
| 16 | 129 | 130 | 131 | 132 | 133 | 134 | 135 | 136 | | 132 |
| 17 | 137 | 138 | 139 | 140 | 141 | 142 | 143 | 144 | | 140 |
| 18 | 145 | 146 | 147 | 148 | 149 | 150 | 151 | 152 | | 148 |
| 19 | 153 | 154 | 155 | 156 | 157 | 158 | 159 | 160 | 161 | 156 |
| 20 | 162 | 163 | 164 | 165 | 166 | 167 | 168 | 169 | | 165 |
| 21 | 170 | 171 | 172 | 173 | 174 | 175 | 176 | 177 | | 173 |
| 22 | 178 | 179 | 180 | 181 | 182 | 183 | 184 | 185 | | 181 |
| 23 | 186 | 187 | 188 | 189 | 190 | 191 | 192 | 193 | 194 | 189 |
| 24 | 195 | 196 | 197 | 198 | 199 | 200 | 201 | 202 | | 198 |
| 25 | 203 | 204 | 205 | 206 | 207 | 208 | 209 | 210 | | 206 |
| 26 | 211 | 212 | 213 | 214 | 215 | 216 | 217 | 218 | | 214 |
| 27 | 219 | 220 | 221 | 222 | 223 | 224 | 225 | 226 | 227 | 222 |
| 28 | 228 | 229 | 230 | 231 | 232 | 233 | 234 | 235 | | 231 |
| 29 | 236 | 237 | 238 | 239 | 240 | 241 | 242 | 243 | | 239 |
| 30 | 244 | 245 | 246 | 247 | 248 | 249 | 250 | 251 | | 247 |
| 31 | 252 | 253 | 254 | 255 | | | | | | 255 |

Fig 3B

```
int decodePalette[ ] = {
                          710            720           730
                           R              G             B
       0xff << 24 |    0 << 16 |    0 << 8 |    0,      Z
       0xff << 24 |    8 << 16 |    8 << 8 |    8,
       0xff << 24 |   16 << 16 |   16 << 8 |   16,
       0xff << 24 |   24 << 16 |   24 << 8 |   24,
       0xff << 24 |   33 << 16 |   33 << 8 |   33,
       0xff << 24 |   41 << 16 |   41 << 8 |   41,
       0xff << 24 |   49 << 16 |   49 << 8 |   49,
       0xff << 24 |   57 << 16 |   57 << 8 |   57,
       0xff << 24 |   66 << 16 |   66 << 8 |   66,
       0xff << 24 |   74 << 16 |   74 << 8 |   74,
       0xff << 24 |   82 << 16 |   82 << 8 |   82,
       0xff << 24 |   90 << 16 |   90 << 8 |   90,
       0xff << 24 |   99 << 16 |   99 << 8 |   99,
       0xff << 24 |  107 << 16 |  107 << 8 |  107,
       0xff << 24 |  115 << 16 |  115 << 8 |  115,
       0xff << 24 |  123 << 16 |  123 << 8 |  123,
       0xff << 24 |  132 << 16 |  132 << 8 |  132,
       0xff << 24 |  140 << 16 |  140 << 8 |  140,
       0xff << 24 |  148 << 16 |  148 << 8 |  148,
       0xff << 24 |  156 << 16 |  156 << 8 |  156,
       0xff << 24 |  165 << 16 |  165 << 8 |  165,
       0xff << 24 |  173 << 16 |  173 << 8 |  173,
       0xff << 24 |  181 << 16 |  181 << 8 |  181,
       0xff << 24 |  189 << 16 |  189 << 8 |  189,
       0xff << 24 |  198 << 16 |  198 << 8 |  198,
       0xff << 24 |  206 << 16 |  206 << 8 |  206,
       0xff << 24 |  214 << 16 |  214 << 8 |  214,
       0xff << 24 |  222 << 16 |  222 << 8 |  222,
       0xff << 24 |  231 << 16 |  231 << 8 |  231,
       0xff << 24 |  239 << 16 |  239 << 8 |  239,
       0xff << 24 |  247 << 16 |  247 << 8 |  247,
       0xff << 24 |  255 << 16 |  255 << 8 |  255
};
```

Fig 7

SYSTEM FOR TRANSMITTING A VIDEO STREAM OVER A COMPUTER NETWORK TO A REMOTE RECEIVER

RELATED APPLICATIONS

This application is a divisional application of U.S. application Ser. No. 09/312,922, filed on May 17, 1999 now U.S. Pat. No. 7,257,158, and entitled "SYSTEM FOR TRANSMITTING VIDEO IMAGES OVER A COMPUTER NETWORK TO A REMOTE RECEIVER".

This application claims priority of U.S. application Ser. No. 09/312,922 and under 35 U.S.C.§119 (e) of U.S. provisional application Ser. No. 60/085,818, filed on May 18, 1998, and entitled "APPARATUS FOR TRANSMITTING LIVE VIDEO IMAGES OVER A COMPUTER NETWORK TO MULTIPLE REMOTE RECEIVERS." The provisional application Ser. No. 60/085,818, filed on May 18, 1998, and entitled "APPARATUS FOR TRANSMITTING LIVE VIDEO IMAGES OVER A COMPUTER NETWORK TO MULTIPLE REMOTE RECEIVERS" is also hereby incorporated by reference.

U.S. application Ser. No. 09/470,566, entitled General Purpose Compression for Video Images (RHN), filed on Dec. 22, 1999, now U.S. Pat. No. 7,016,417, claimed priority based on U.S. provisional application Ser. No. 60/113,276 filed on Dec. 23, 1998, and entitled "METHOD OF IMAGE ENHANCEMENT, COMPRESSION, AND ENCODING of GRAYSCALE IMAGES (ECHOCODEC)." A divisional application, U.S. application Ser. No. 11/280,656, was filed on Nov. 15, 2005, and published as U.S. publication 2006/0067408 on Mar. 30, 2006.

FIELD OF THE INVENTION

This invention relates to the field of communications systems. More particularly, this invention relates to the field of video communications systems.

BACKGROUND OF THE INVENTION

In the last decade, there have been tremendous advances in medical devices that have greatly improved the ability to diagnose and treat patients. Ultrasounds, sonograms, echocardiograms, and angioplastigrams are just a few modern tools developed to accurately diagnose patients with coronary problems, kidney stones, tumors, and other diseases without conducting risky and expensive exploratory surgeries. These tools are especially useful because they have the capability of being more accurate than exploratory surgeries and do not pose an additional risk to patients.

Given the benefits of ultrasounds, sonograms, echocardiograms, and angioplastigrams, these tools are in widespread use in many hospitals, clinics, testing facilities, and individual doctors' offices. Many doctors primarily base their diagnosis on the results from ultrasounds, sonograms, echocardiograms, and angioplastigrams. While these tools allow doctors to make their diagnosis without costly, risky, and time consuming exploratory surgeries, an error in administering an ultrasound, sonogram, echocardiogram, and angioplastigram can lead to a wrong diagnosis. A wrong diagnosis can be catastrophic for the patient. By receiving an incorrect diagnosis, the patient can potentially fail to receive needed medical treatment and/or be unnecessarily treated. Whether needed medical treatment is withheld or unnecessary medical treatment is given due to an erroneous test result from an ultrasound, sonogram, echocardiogram, or angioplastigram, the patient unnecessarily suffers.

While ultrasounds, sonograms, echocardiograms, and angioplastigrams are extremely useful tools to diagnose ailments in patients, any of these tools administered in an imprecise manner or in a wrong location will most likely produce a wrong result. This wrong result typically leads to the wrong diagnosis. Learning proper techniques and procedures in order to produce a correct result from an ultrasound, sonogram, echocardiogram, or angioplastigram requires extensive specialized training and many years of medical training. People who possess such specialized knowledge in administering ultrasounds, sonograms, echocardiograms, and angioplastigrams are in short supply and only administer a fraction of these tests that are performed each year. Instead, technicians with limited medical knowledge and limited training typically administer these tests. By not properly administering these tests, the results are often times inaccurate and lead to the wrong diagnosis. Furthermore, the tests are typically performed and later reviewed by the doctor after the patient has left the technician's office.

In order to achieve a higher accuracy rate, close supervision by a specially trained person is needed while a technician administers any one of these tests. However, having such a specially trained person at each of these tests while they are being administered is typically impractical and would result in much higher medical costs.

SUMMARY OF THE INVENTION

A method of and apparatus for transmitting video images preferably allows a specially trained individual to remotely supervise, instruct, and observe administration of medical tests conducted at remote locations. This apparatus preferably includes a source device, a transmitting device, and at least one remote receiving device. Preferably, the transmitting device and the remote receiving device communicate over a network such as the Internet Protocol network. Alternatively, the transmitting device and the receiving device communicate over any appropriate data network. The transmitting device transmits the video images to the remote receiving device either for live display through the source device or for pre-recorded display through a video recorder device. The remote receiving device is also capable of communicating with the transmitting device while simultaneously receiving video images. The source device is preferably a medical test device such as an ultrasound, a sonogram, an echocardiogram, an angioplastigram, and the like. This medical test device preferably generates video images for the transmitting device. The transmitting device captures the video images in real-time from the source device and compresses these video images utilizing a compression method prior to transmitting data representing the video images to the remote receiving device. Remote users utilizing the remote receiving devices are capable of remotely controlling a number of parameters relating to the source device and the transmitting device. Such parameters include compression method, image quality, storage of the video images on the transmitting device, manipulating and controlling the source device, and the like.

BRIEF DESCRIPTION OF THE DRAWINGS

FIG. 3A illustrates software code utilized during a compression process of the present invention.

FIG. 3B illustrates a look-up table representing the software code utilized during the compression process of the present invention.

FIG. 7 illustrates software code utilized during a decompression process of the present invention.

FIG. 8A-1 illustrates a flow chart showing the steps for transmitting a stream of video images.

FIG. 8A-2 illustrates an alternate flow chart showing the steps for transmitting a live stream of video.

DETAILED DESCRIPTION OF THE INVENTION

Figure 1:
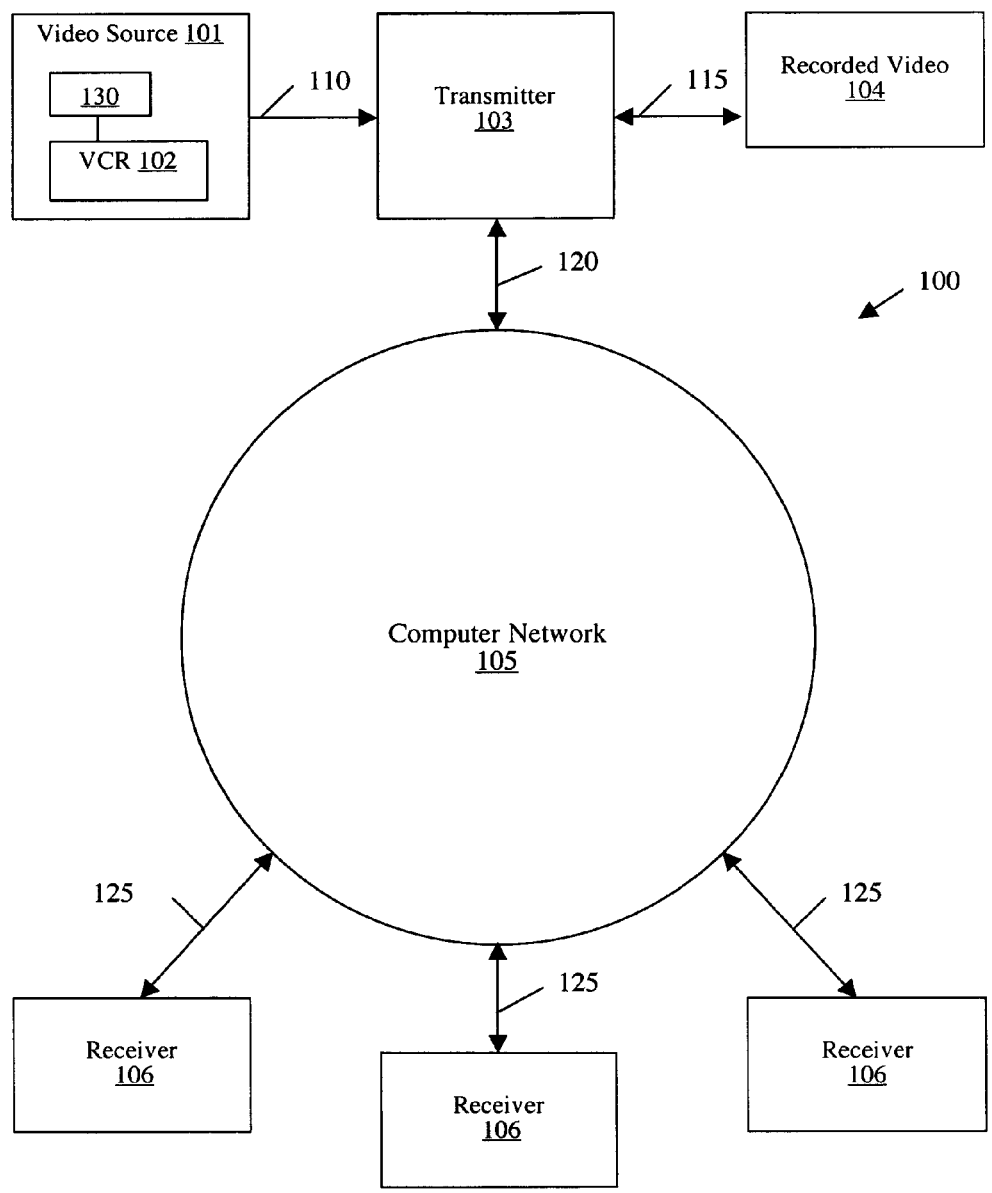
FIG. 1 illustrates a block diagram of a preferred embodiment of the present invention.

FIG. 1 illustrates a video system 100 according to the present invention for transmitting video images from one location to another. The video system 100 preferably includes a video source 101, a video cassette recorder 102, a transmitter 103, a recorded video device 104, a computer network 105, a plurality of receivers 106, and data links 110,115,120, and 125. Preferably, the video source 101 includes the video cassette recorder 102 and is coupled to the transmitter 103 via the data link 110. The data link 110 is preferably a Super-Video (S-Video) connection. The transmitter 103 is also preferably coupled to the recorded video device 104 and the computer network 105 via the data links 115 and 120, respectively.

Preferably, the plurality of receivers 106 are coupled to the computer network 105 via the data links 125. Each of the plurality of receivers 106 are preferably a computer system having a display, central processing unit, and input device. The data links 125 preferably link each of the plurality of receivers 106 to the computer network 105. The data links 125 include any appropriate connection to the computer network 105 including Ti communication lines, DSL links, cellular links, microwave transmission, land lines, twisted pair cable, and the like. The video system 100 shown in FIG. 1 is merely illustrative and is only meant to show the preferred embodiment of the present invention.

In alternate embodiments, additional transmitters, video sources, and receivers could be included without departing from the spirit and scope of the video system 100.

Additionally, in an alternate embodiment, the transmitter 103 is included within the computer network 105 and functions as a server within the computer network 105.

The video source 101 preferably provides the video system 100 with at least one video image. The video source 101 is capable of providing either a live video image or a pre-recorded video image. For example, to provide a live video image, the video source 101 preferably includes a real-time input device 130. This real-time input device 130 is preferably a medical measurement device such as an ultrasound, sonogram, echocardiogram, angioplastigram, and the like. Alternatively, this real-time input device 130 could be any other appropriate image capturing device including a video camera and a still camera. The pre-recorded video image is preferably provided by the video cassette recorder 102. Preferably, the video cassette recorder 102 is configured to record the real-time video images produced by the real-time input device 130 and play these pre-recorded video images at a later time. In addition to recording live video images and re-playing them, the video cassette recorder 102 is also preferably configured to accept and play a pre-recorded video cassette tape. The video source 101 is preferably configured to transfer the video image to the transmitter 103 via the data link 110.

The recorded video device 104 is preferably coupled to the transmitter 103 via the data link 115. Preferably, the recorded video device 104 stores video images received by the transmitter 103 for playback at a later time. The recorded video device 104 allows the transmitter 103 to distribute these video images to the plurality of receivers 106 at a later time. In addition, the recorded video device 104 also preferably serves as a mass storage device to store data that is unrelated to the video images.

The transmitter 103 preferably controls the flow of video images from both the video source 101 and the recorded video component 104 over the computer network 105 to any number of the plurality of receivers 106. Preferably, the transmitter 103 compresses the video images prior to transmission to one of the plurality of receivers 106, as will be described in detail below. Further, the transmitter 103 preferably monitors and selectively establishes connections with the computer network 105 over the data link 120.

In the video system 100, the computer network 105 is preferably an Internet Protocol network. In alternate embodiments, the computer network 105 is any appropriate data network. The computer network 105 is configured to transmit information between the plurality of receivers 106 and the transmitter 103 via the data links 125 and 120, respectively.

The plurality of receivers 106 are preferably configured to selectively receive a stream of video images from the transmitter 103 via the data link 120, the computer network 105, and the appropriate data link 125. For example, at least one of the plurality of receivers 106 is programmed to receive the stream of video images from the transmitter 103. Accordingly, only the selected ones of the plurality of receivers 106 are capable of receiving the stream of video images from the transmitter 103. In addition to receiving the stream of video images, the selected ones of the plurality of receivers 106 are also capable of transmitting instructions to the transmitter 103 via the data link 125, the computer network 105, and the data link 120.

Figure 2:
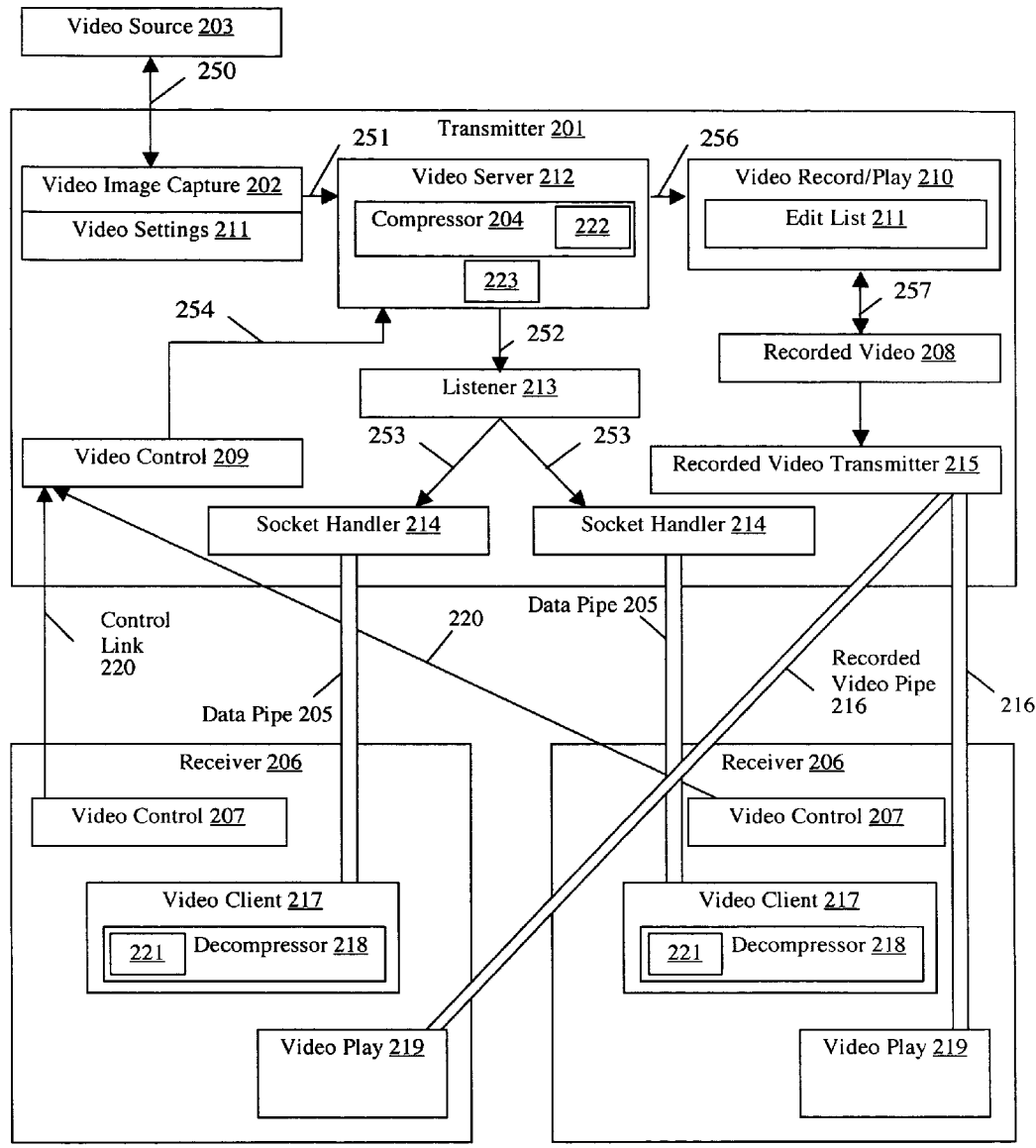
FIG. 2 illustrates a data flow diagram of the preferred embodiment of the present invention.

FIG. 2 illustrates a data path diagram of the preferred embodiment of the present invention. FIG. 2 shows a video system 200 that is similar to the video system 100 shown in FIG. 1. The video system 200 preferably includes a transmitter 201, a video source 203, and a plurality of receivers 206. The video system 200 shown in FIG. 2 is merely illustrative and is meant to show the preferred embodiment of the present invention. In alternate embodiments, additional components such as transmitters, video sources, and receivers are included without departing from the spirit and scope of the video system 200.

Preferably, the video source 203 is coupled to the transmitter 201 via a data link 250. Upon direction from the transmitter 201, the video source 203 is preferably configured to supply the transmitter 201, through a video image capture device 202, with a stream of video images through the data link 250.

The transmitter 201 preferably includes the video image capture device 202, a video server 212, a video controller 209, a listener device 213, a recorded video transmitter 215, and a plurality of socket handlers 214. The video image capture device 202 also preferably includes a plurality of video settings 211 configured by the user.

Preferably, the video image capture device 202 receives a stream of video images from the video source 203 and then transmits this stream of video images to the video server 212 via a data link 251. The plurality of video settings 211 preferably allow adjustments to be made for modifying the stream of video images received by the video server 212.

Examples of adjustments included within the plurality of video settings 211 include brightness, contrast, hue, and the like.

The video server 212 preferably includes a compressor 204 and a buffer 223. As the stream of video images are received by the video server 212, the compressor 204 is configured to compress the stream of video images thereby creating a compressed stream of video images. As this compressed stream of video images is generated, the compressor 204 transmits each data block into the buffer 223. Once the buffer 223 holds the compressed stream of video images having a predetermined number of data blocks, the compressed stream of video images is transmitted to one or more of the plurality of receivers 206. The compressor 204 preferably utilizes a lossless compression method to form the compressed stream of video images, as will be discussed in detail below. The compressor 204 preferably includes a buffer 222 for use with the compression method.

In an alternate embodiment, the compressor 204 utilizes a lossy compression method to compress the flow of video images.

The video recorder 210 is capable of storing the stream of video images received by the transmitter 201 for transmission to one or more of the plurality of receivers 206 at a later time. Preferably, the stream of video images is compressed by the compressor 204 before being stored by the video recorder 210.

In order to transmit the compressed stream of video images in real-time, the transmitter preferably transmits the compressed stream of video images through the listener device 213. The listener device 213 is preferably configured to couple to the video server 212 via a data link 252. Preferably, the listener device 213 is also coupled to the plurality of socket handlers 214 via the data links 253 and monitors the plurality of socket handlers 214 for any connection requests. Upon receiving a connection from appropriate ones of the plurality of receivers 206 through a socket handler 214, the listener device 213 preferably informs the video server 212 via the data link 252. In order to transmit the stream of video images to the appropriate ones of the plurality of receivers 206, one of the plurality of socket handlers 214 couples to each of the appropriate ones of the plurality of receivers 206. The connection(s) between the plurality of socket handlers 214 and the appropriate ones of the plurality of receivers 206 is (are) preferably formed through the computer network 105 (FIG. 1).

In order to transmit the stream of video images at a later time, the video recorder 210 preferably stores the stream of video images. The video recorder 210 preferably includes an edit list 211 and is coupled to the video server 212 through a data link 256.

The video recorder 210 is also coupled to a recorded video transmitter 215 through a data link 257. The video recorder 210 is preferably configured to control the initiation and termination of storing the stream of video images in response to instructions received by the video controller 209. The recorded video device 208 is preferably a storage device coupled to the video recorder 210 and configured to store the stream of video images.

Thus, the recorded video device 208 allows the video system 200 to save the stream of video images originating from the video source 203 and allows the video system 200 to transmit this saved stream of video images to appropriate ones of the plurality of receivers 206 at a later time. The recorded video device 208 is preferably coupled to the recorded video transmitter 215 and configured to transmit the saved stream of video images from the transmitter 201 to the appropriate ones of the plurality of receivers 206 over the appropriate recorded video pipe(s) 216.

The plurality of receivers 206 preferably reside in a remote location relative to the transmitter 201. Preferably, the plurality of receivers 206 selectively receive the flow of video images from the transmitter 201 and also selectively respond to the transmitter 201 with instructions.

Each of the plurality of receivers 206 preferably includes a video controller 207, a video client 217, and a video play device 219. The video controller 207 preferably communicates with the video controller 209 of the transmitter 201 via a data link 220.

Preferably, the video controller 207 relays information regarding the frame size, frame rate, compression method, and other parameters being transmitted to the video controller 207 via the data link 220. Thus, a user interfacing with one of the plurality of receivers 206 is able to modify the frame size, frame rate, compression method, and other parameters of the incoming stream of video images to one of the plurality of receivers 206. Since the plurality of receivers 206 and the transmitter 201 are preferably located in remote locations, by interfacing with the video controller 207, the user is able to remotely control video parameters such as frame size, frame rate, compression method, and the like which are included within the video settings 211 at the transmitter 201.

In one embodiment, the socket handler 214 selectively transmit data to each respective receiver 206 at different frame rates by skipping (dropping) frames to the slower receiver 206 or based on a different, slower frame rate requested by one of the users.

When receiving the compressed stream of video images in real-time from the video server 212 in the transmitter 201, the video client 217 in the receiver 206 preferably receives the compressed stream of video images. The video client 217 preferably includes a decompressor 218 that is configured to decompress the compressed stream of video images to form a representation of the original, uncompressed stream of video images.

After the compressed stream of video images is processed by the decompressor 218, the resulting stream of video images is ready to be displayed. The decompressor 218 preferably includes a buffer 221 that is utilized with the decompression process.

When receiving the stored stream of video data at a later time from the recorded video device 208 in the transmitter 201, the video play device 219 preferably receives the stored stream of video data and allows the representative stream of video images to be displayed. Before being displayed, the stored stream of video data is decompressed by the decompressor 218 in order to form a representation of the original, uncompressed stream of video images.

Various procedures for monitoring the video data that is received by the plurality of receivers 206 for errors are disclosed in the provisional application that is included by reference or are otherwise apparent to those skilled in the art. Such errors can include faulty compression, faulty decompression, missing video data, delayed video data, and the like. Further, it is also disclosed in the provisional application or is otherwise apparent to those skilled in the art to alert and notify users of the appropriate plurality of receivers 206, the transmitter 201, and the source device 203 when any of these errors occur. In order to avoid unnecessarily complicating the discussion of the video system 200, some of the specific details of the error detection and notification are not discussed.

In operation, the transmitter 201 acts as a server that is connected to an appropriate data network. Preferably, each of the plurality of receivers 206 individually acts as a standalone computer system connected to the data network. The transmitter 201 selectively enables a data stream of video images to be transmitted to an appropriate one or more of the plurality of receivers 206. In order for a particular receiver 206 to receive the data stream of video images from the transmitter 201, the receiver 206 logs onto the computer network 105 (FIG. 1). Preferably, the computer network 105 is the Internet Protocol network. Alternatively, the computer network 105 is any appropriate data network. Typically, in the preferred embodiment, this log on is accomplished by connecting through an Internet service provider. A connection between the transmitter 201 and the particular receiver 206 is preferably established through the computer network 105 (FIG. 1). The particular receiver 206 preferably communicates with the transmitter 201 over the computer network 105 and furnishes a user identification, a password, or another form of identification and verification. Once the transmitter 201 identifies the particular receiver 206 as an approved user, the transmitter 201 allows the data stream of video images to be transmitted to the particular receiver 206. The transmitter 201 is capable of simultaneously transmitting the data stream of video images to multiple receivers 206.

Figures 1, 8A:
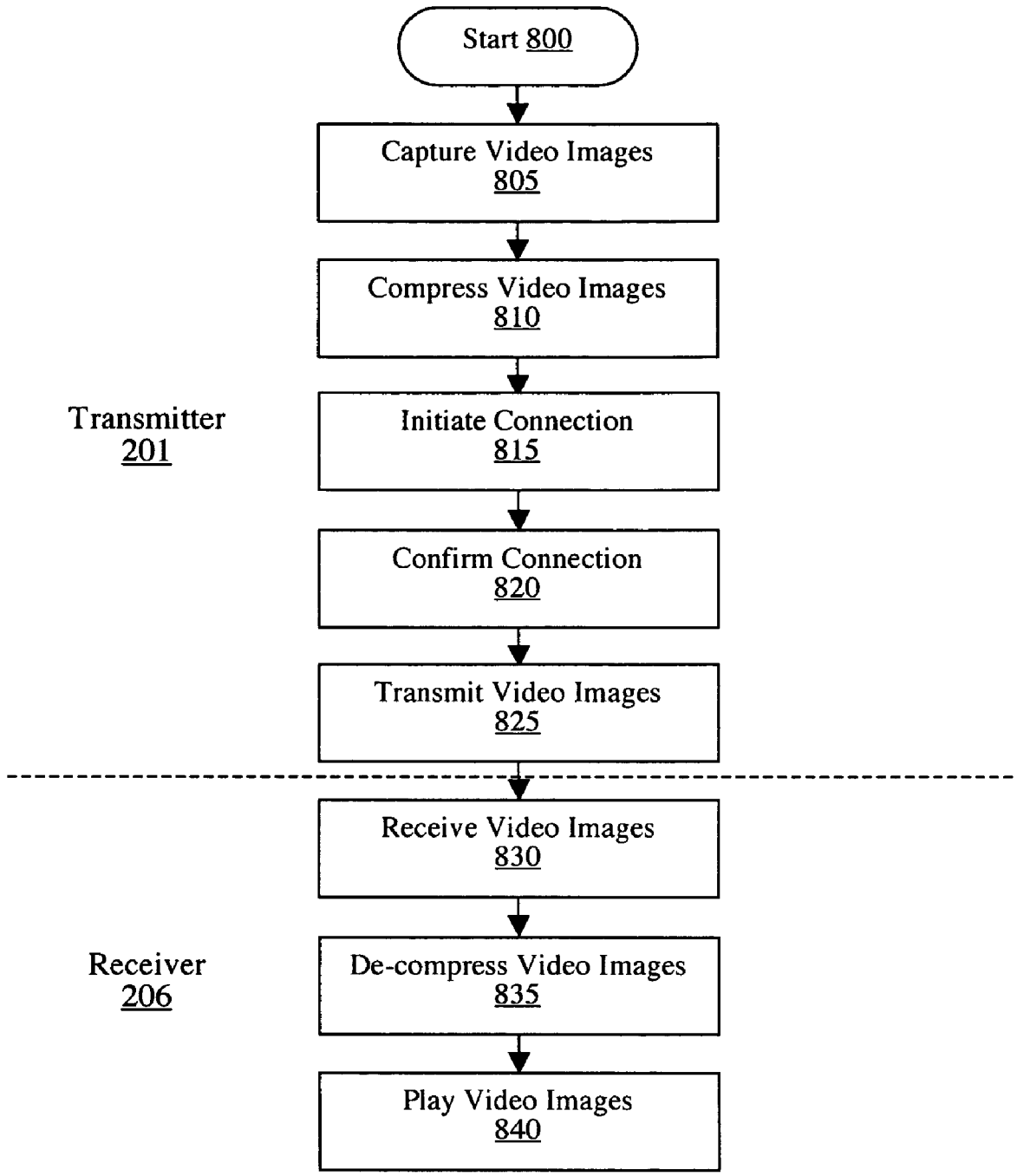
Figures 2, 8A:
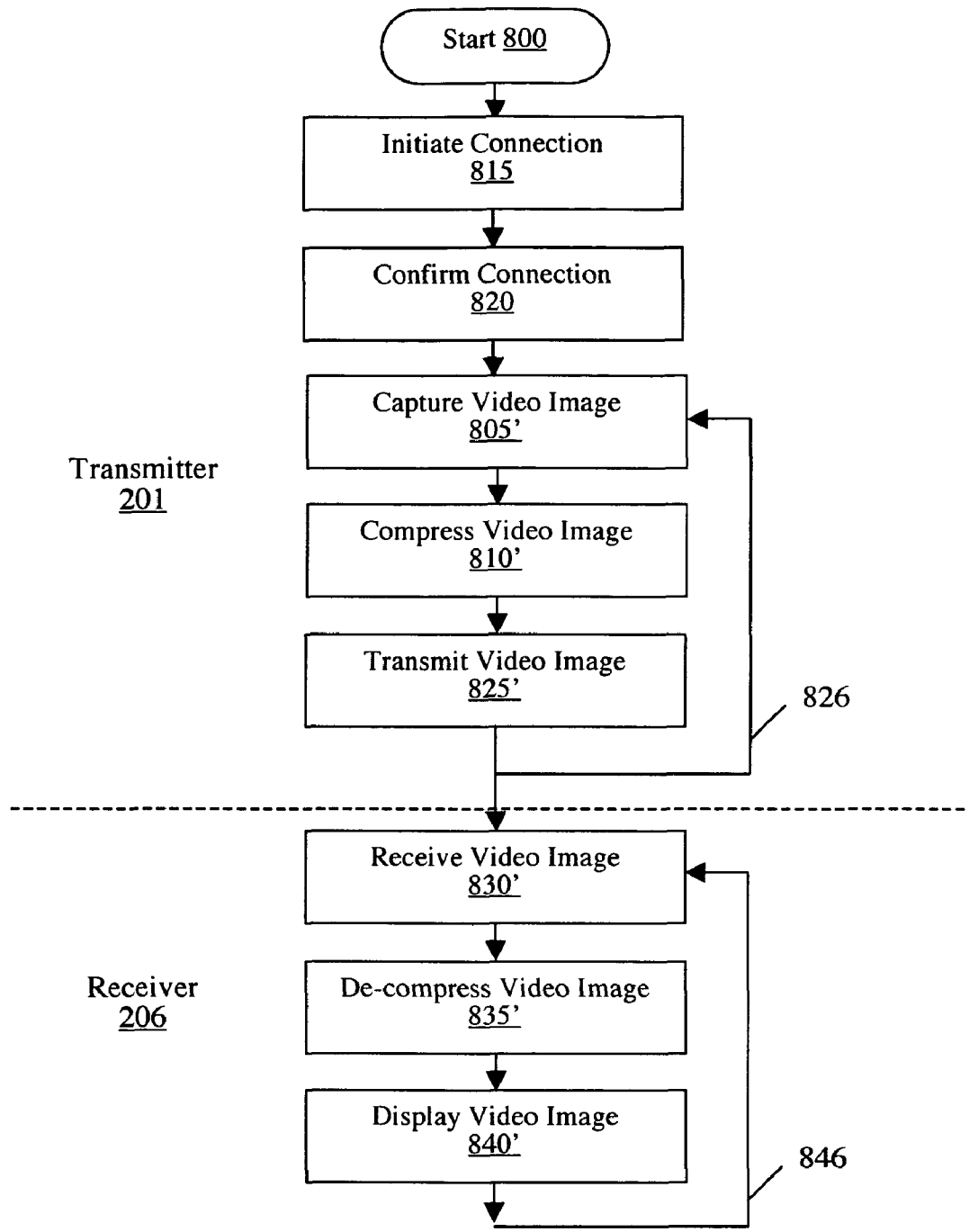

FIG. 8A-1 illustrates a flow chart showing the steps involved when transmitting a stream of video images from the transmitter 201 (FIG. 2) to one or more of the plurality of receivers 206. The steps 800-825 preferably occur within the transmitter 201 (FIG. 2). The steps 830-840 preferably occur within one of the plurality of receivers 206 (FIG. 2). The process of transmitting the stream of video images from the transmitter 201 to one of the plurality of receivers 206 (FIG. 2) begins at the step 800.

Next, the stream of video images from the video source 203 are captured in the video image capture device 202 (FIG. 2) in the step 805. In the step 810, the stream of video images, captured by the video image capture device 202, is compressed by the compressor 204 (FIG. 2) within the video server 212 (FIG. 2). Next, in the step 815, a connection between one of the plurality of socket handlers 214 (FIG. 2) and one of the plurality of receivers 206 (FIG. 2) is initiated. In the step 820, the connection between the transmitter 201 (FIG. 2) and one of the plurality of receivers 206 (FIG. 2) is confirmed by the listener device 213 (FIG. 2). Next, the compressed stream of video images is transmitted to an appropriate one or more of the plurality of receivers 206 (FIG. 2) in the step 825.

In the step 830, the appropriate one or more of the plurality of receivers 206 (FIG. 2) receives the compressed stream of video images from the transmitter 201. Next in the step 835, the compressed stream of video images is decompressed by the decompressor 218 (FIG. 2). Finally, the stream of video images is displayed for the user by one of the plurality of receivers 206 (FIG. 2) in the step 840.

The present invention is not limited by the order of steps shown in FIG. 8A-1. For example, FIG. 8A-2 illustrates an alternate flow chart showing the steps involved when transmitting a live stream of video.

In FIG. 8A-2, the process of transmitting the live stream of video from the transmitter 201 to one of the plurality of receivers 206 (FIG. 2) begins at the step 800. As discussed above, a particular receiver 206 preferably first communicates with the transmitter 201 over the computer network 105 to initiate a connection, at step 815 of FIG. 8A-2, and furnishes a user identification, a password, or another form of identification and verification. Once the transmitter 201 identifies the particular receiver 206 as an approved user, the connection is confirmed at step 820. A data pipe 205 (FIG. 2) is established between the approved receiver 206 and the transmitter 201. Additionally, the remote control mechanism is established between the remote receiver 206 and the transmitter 201, preferably via control link 220 (FIG. 2).

For each frame of the live stream of video from the video source 203, the pixels for a current frame are captured in the video image capture device 202 (FIG. 2) in the step 805'. In the step 810', the pixels of the current frame are compressed by the compressor 204 (FIG. 2) within the video server 212 (FIG. 2). Next, the compressed data from the current frame is transmitted to an appropriate one or more of the plurality of receivers 206 in the step 825'. Steps 805', 810' and 825' are repeated for each successive frame by looping via path 826. Preferably, if any of the steps 805', 810' or 825' cannot be completed in a time accurate manner, the frame is skipped and the next frame is processed starting at step 805'. Preferably, if the transmitter 201 skips the transmission of any frame, a frame dropped indicator is sent to any affected receiver 206.

In the step 830', the appropriate one or more of the plurality of receivers 206 receives the compressed data for the current frame from the transmitter 201. Next in the step 835', the compressed data is decompressed by the decompressor 218 (FIG. 2). Finally, the decompressed frame of the live video is displayed for the user by one of the plurality of receivers 206 in the step 840'. Steps 830', 835' and 840' are repeated for each frame by looping via path 846. Preferably, if any of the steps 830', 835' and 840' cannot be completed in a time accurate manner, the frame is skipped and the next frame is processed starting at step 830'. Preferably, if the transmitter 201 sent the frame dropped indicator, or the receiver 206 skips the display of any frame, information regarding performance, dropped frames, and the network connection is displayed to the user.

Figure 8B:
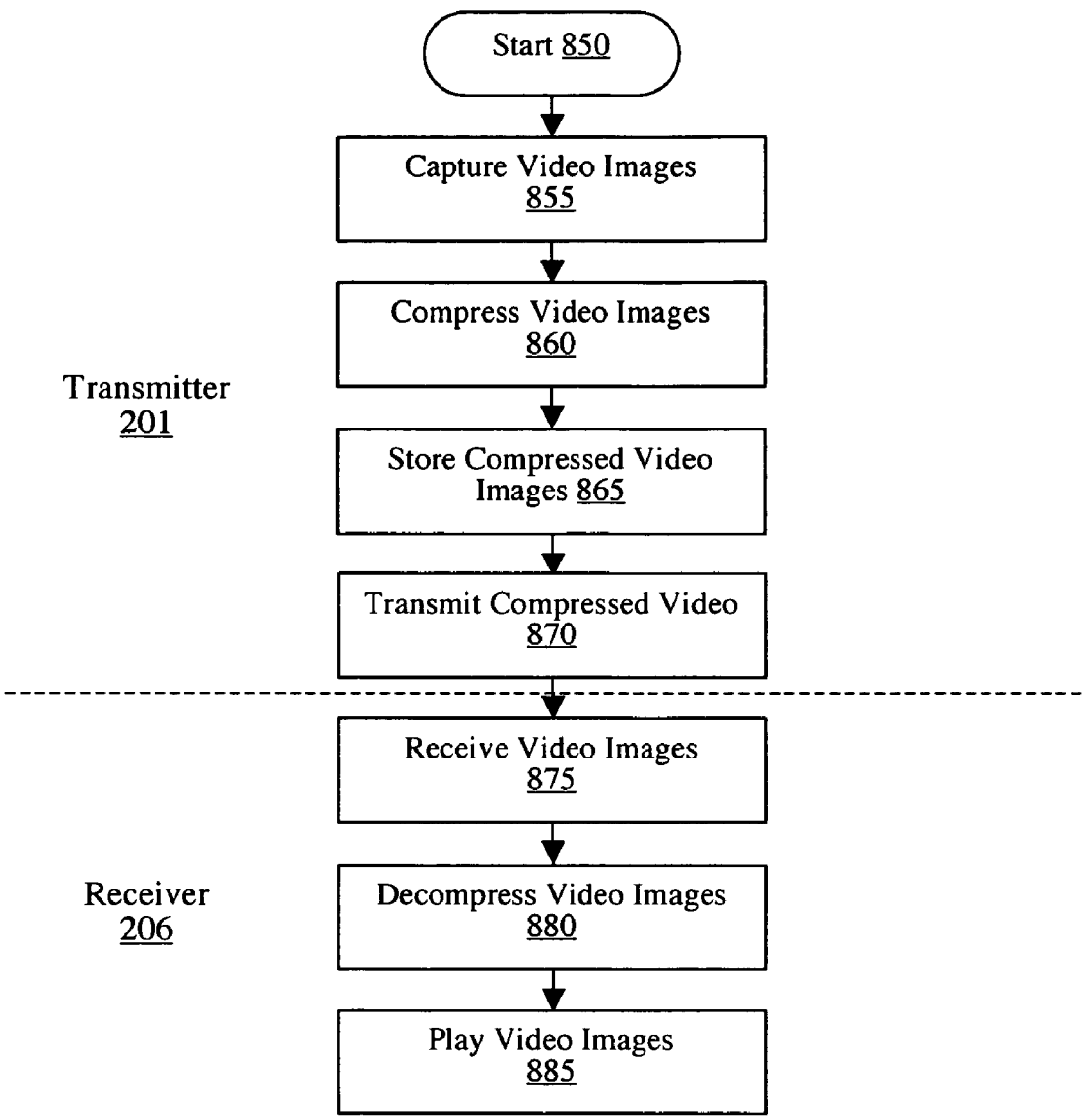
FIG. 8B illustrates a flow chart showing the steps for transmitting a pre-recorded stream of video images.

FIG. 8B illustrates a flow chart showing the steps involved when transmitting a stream of pre-recorded video images from the transmitter 201 to one of the plurality of receivers 206. The steps 850-870 preferably occur within the transmitter 201 (FIG. 2).

The steps 875-885 preferably occur within one of the plurality of receivers 206 (FIG. 2).

The process of transmitting the pre-recorded stream of video images to one of the plurality of receivers 206 (FIG. 2) begins at the step 850. Next, the stream of video images are captured in the video image capture device 202 (FIG. 2) in the step 855. In the step 860, the stream of video images are then compressed by the compressor 204 (FIG. 2) within the video server 212 (FIG. 2). Next, in the step 865, the compressed stream of video images is stored within the recorded video device 208 (FIG. 2), thus forming a pre-recorded and compressed stream of video images. This pre-recorded and compressed stream of video images is capable of being stored indefinitely and transmitted to one of the plurality of receivers 206 (FIG. 2) at any time. Next, the step 870 represents the steps 815, 820, and 825 from FIG. 8A-1, and is utilized to transmit the pre-recorded and compressed stream of video images to one of the plurality of receivers 206 (FIG. 2). A resulting connection between one of the plurality of socket handlers 214 (FIG. 2) and one of the plurality of receivers 206 (FIG. 2) is initiated in the step 870. Additionally in the step 870, the connection between the transmitter 201 (FIG. 2) and one of the plurality of receivers 206 (FIG. 2) is confirmed by the listener device 213 (FIG. 2).

The pre-recorded and compressed stream of video images is also transmitted to one or more of the plurality of receivers 206 (FIG. 2) in the step 870.

In the step 875, the appropriate one or more of the plurality of receivers 206 (FIG. 2) receives the pre-recorded and compressed stream of video images. Next, in the step 880, the pre-recorded and compressed stream of video images is decompressed by the decompressor 218 (FIG. 2). The stream of video images is then displayed to the user by one of the plurality of receivers 206 (FIG. 2) in the step 885.

FIG. 3A illustrates software code which is preferably utilized to perform compression of a stream of video data within the compressor 204 (FIG. 2). This software code includes a lookup table 310 with storage locations representing illumination intensity values from 0 to 255. Each representative storage location includes a line number from 0 to 31 that is indexed to a decompression lookup table. The compression lookup table 310 allows an eight bit entry representing values from 0 to 255 to be compressed into a five bit value. When provided with an illumination intensity value, the line number stored in the corresponding location within the compression lookup table 310 is read and provided as the compressed five bit illumination intensity value.

Documentation 320 is utilized to more clearly illustrate the function of each line contained within the compression lookup table 310. If the illumination intensity value is two (on a scale of 0 to 255), the line number zero stored at the storage location corresponding to this illumination intensity value is read from the compression lookup table 310. As can be seen from the compression lookup table 310, any illumination intensity value between zero to four has a corresponding five bit line number of zero (on a scale of 0 to 31). In a further example, if the illumination intensity value is eighty, the line number ten stored at the storage location corresponding to this illumination intensity value is read from the compression lookup table 310. Instead of transmitting an eight-bit value of 0 to 255 that corresponds to an illumination intensity value of a pixel, the compression lookup table 310 is utilized to compress the eight bit illumination intensity value into a corresponding five bit line number value between 0 and 31.

This compression process is preferably optimized to compress data representing a stream of video images that originates from the video source 203 (FIG. 2) and is received by the transmitter 201 (FIG. 2). In practice, this data representing the stream of video images is transmitted in terms of a stream of pixel data. A predetermined number of pixels represent each video frame within the stream of video images. Further, each pixel is represented by illumination intensity values relating to a red scale, a green scale, and a blue scale. Each of the red scale, green scale and blue scale have illumination intensity values which range from 0 to 255. For each pixel, the illumination intensity value of zero represents a fully off state, and the illumination intensity value of "255" represents a fully on state.

To achieve a gray scale or black and white image, each pixel within the black and white image has the same illumination intensity value for the red, green, and blue scales.

In the preferred embodiment, the stream of video images are displayed as "black and white" images that are defined by a gray-scale having 256 shades of gray. This optimizes the compression of the video data and recognizes that full color is not necessary for good quality video images from the medical measurement devices utilized with the preferred embodiment of the present invention. Because only black and white images are utilized, the compression process preferably utilizes the intensity values for only one color component, for example, the blue scale to represent each pixel. These illumination intensity values are modified within the compressor 204 (FIG. 2) before being transmitted to one of the plurality of receivers 206 (FIG. 2) or stored in the video recorder 210, as described above. Alternatively, as will be apparent to those skilled in the art, full color is achieved by separately compressing and transmitting the red, green, and blue values.

In the preferred embodiment, to achieve black and white video images, the intensity values for the other two color components, for example, the red and green scales are neither compressed nor transmitted. To achieve black and white video images, it is sufficient to compress and transmit only one color component, for example, the blue scale value for each pixel. At a later time after transmission and decompression of the blue scale value for each pixel, to display each pixel in terms of a gray scale, the red scale and the green scale values for a particular pixel are generated from the blue scale value.

Alternate embodiments of the present invention are capable of utilizing either the green scale or the red scale value to represent each pixel. Further, alternate embodiments utilizing video images displayed in color compress and transmit the red scale, green scale, and blue scale value.

FIG. 3B illustrates a lookup table 350. This look-up table 350 shows a logical representation of the compression process according to the compression lookup table 310 shown in FIG. 3A, for illustrative purposes only. The lookup table 350 classifies an eight bit illumination intensity value for a pixel into an appropriate level within a reduced level index representing the five bit line number. There are preferably 32 levels within this reduced level index, from 0 to 31, which are represented by the rows 0 to 31 on the left of the table 350. Each line number corresponds with one of the levels within the reduced level index. The lookup table 350 also includes 10 columns, which are represented by letters "A" through "J". The entries within columns "A" through "I" represent the illumination intensity value for the pixel and correspond to the storage locations within the lookup table 350. Each of the illumination intensity values is compressed into the line number of the row on which the illumination intensity value is found within the table 350.

The entries within column "J" represent an average illumination intensity level associated with each line number, which will be discussed below in relation to the decompression lookup table. This average illumination intensity level falls within a range of a lowest and highest illumination intensity value within the particular row.

As a further example of the pixel data compression technique of the present invention utilizing the lookup table 350 when provided with pixel data having an illumination intensity value of 167, the line number 20 is provided as the compressed value from the compression lookup table. Any pixel having an illumination intensity value between 162 and 169 corresponds to the line number 20 in the lookup table 350.

Accordingly, for pixels having illumination intensity values between and including 162 and 169, the five bit line number 20 is provided as the compressed value, which is either stored by the recorded video device 208 or transmitted by the transmitter 201 to one or more of the receivers 206.

Figure 5A:
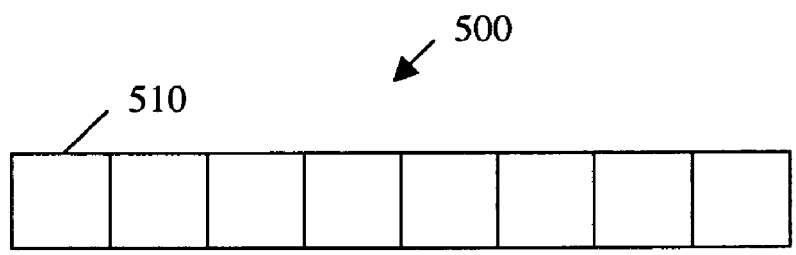
FIG. 5A illustrates a data structure of the present invention.

FIG. 5A illustrates a data structure 500 having 8 bits of storage. An identification bit 510 is preferably a leading bit within the data structure 500. This identification bit 510 signals whether the particular data structure contains a line number representing the illumination intensity level or a repeat value representing a number of times to repeat an illumination intensity value of a prior pixel. The data structure 500 is used to carry both compressed line number values and the repeat value for compressed strings of similar pixels.

Figure 5B:
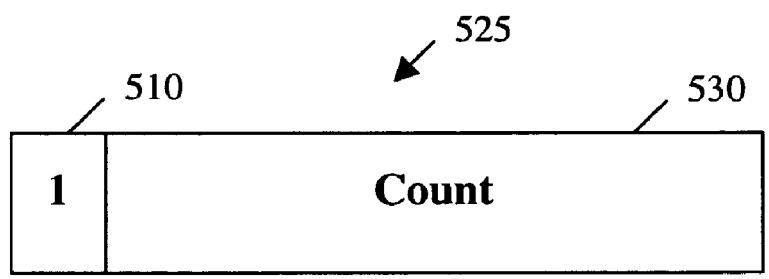
FIG. 5B illustrates the data structure configured to transmit a repeat command for the preferred embodiment.

FIG. 5B illustrates a data structure 525 used to transmit the repeat value, which has a specific configuration of the data structure 500 (FIG. 5A). To signal that this data structure 525 is transmitting a repeat value, the identification bit 510 includes a value corresponding to a logical one. The number of times to repeat is preferably stored in the seven remaining bits 530. By storing a logical one in the identification bit 510, the decompressor 218 (FIG. 2) is instructed while decoding to repeat the line number of the previous pixel a number of times corresponding to the seven bit repeat value. In this preferred embodiment, the repeat counter value is limited to a value of 127, which is the maximum number capable of being expressed by seven bits. Alternatively, the repeat counter value can be represented by any appropriate number of bits.

Figure 5C:
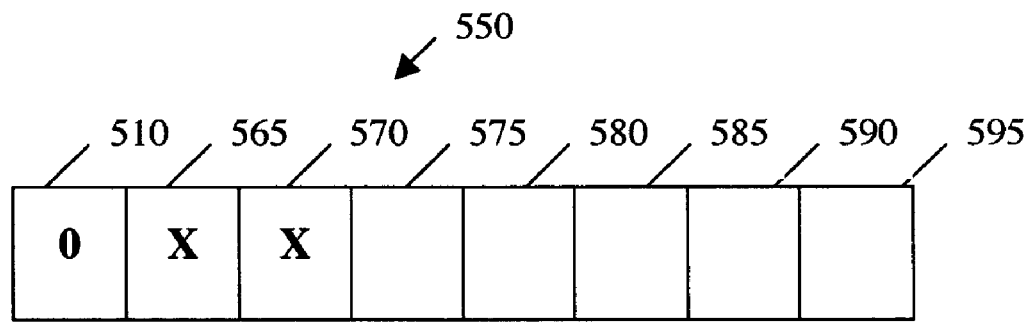
FIG. 5C illustrates the data structure for the preferred embodiment configured to transmit a line number that represents a pixel illumination intensity level.

FIG. 5C illustrates a data structure 550 used to transmit a line number, which has a specific configuration of the data structure 500 (FIG. 5A). To signal that this data structure 550 is transmitting a compressed line number, representing an illumination intensity value of a pixel, the identification bit 510 includes a value corresponding to a logical zero. The data structure 550 is configured to transmit the line number that represents the illumination intensity level of the pixel. Preferably, the bits 565 and 570 are unused. The bits 575-595 represent the five bit line number corresponding to the illumination intensity value from the compression lookup table 310 (FIG. 3A). By setting the identification bit 510 to a logical zero, the decompressor 218 (FIG. 2) recognizes that information held in the five bits 575-595 represents the line number corresponding to the illumination intensity value of a pixel in the data stream.

Figure 4A:
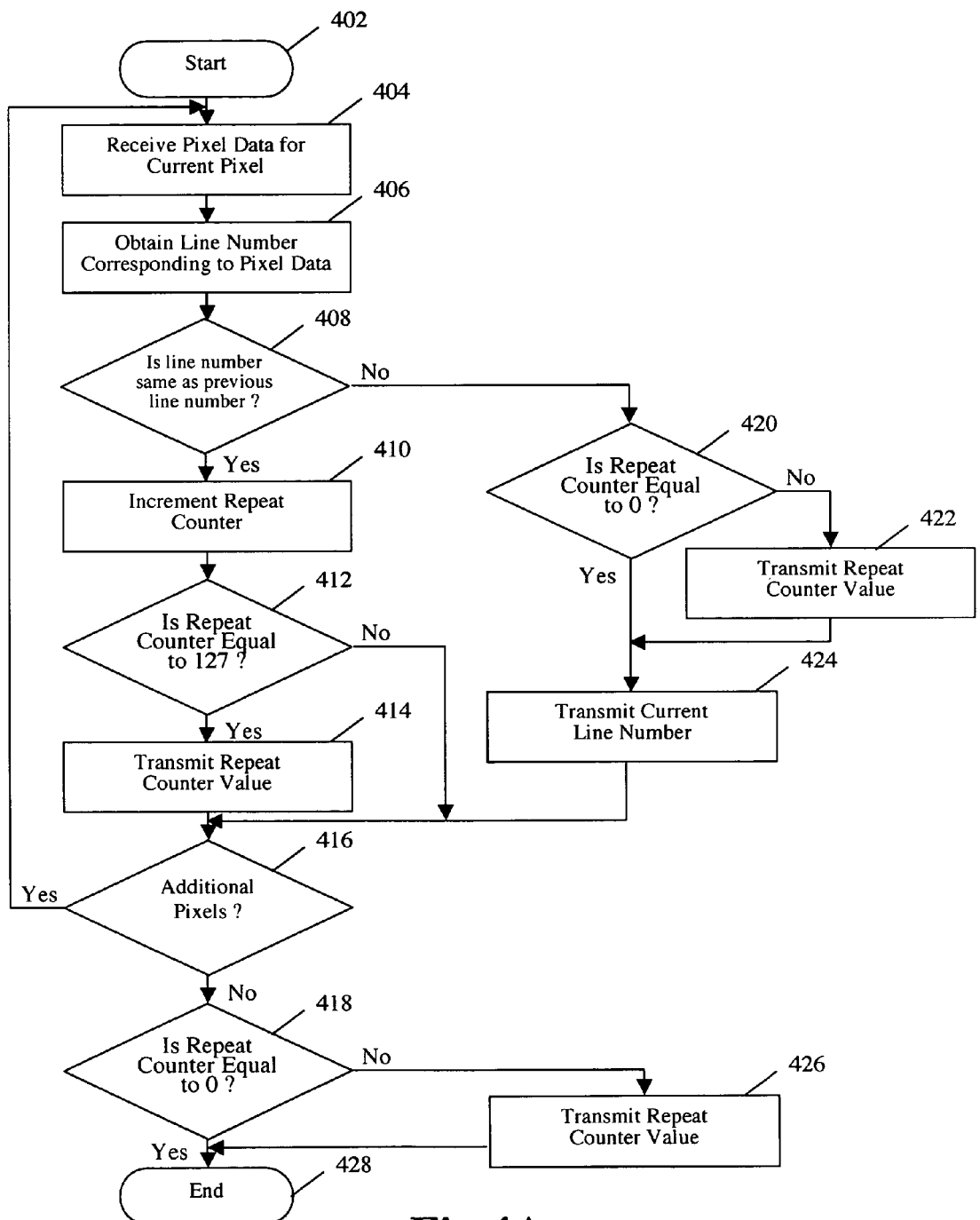
FIG. 4A illustrates a flow chart showing the steps involved in the compression process within a compressor of the preferred embodiment.
Figure 4B:
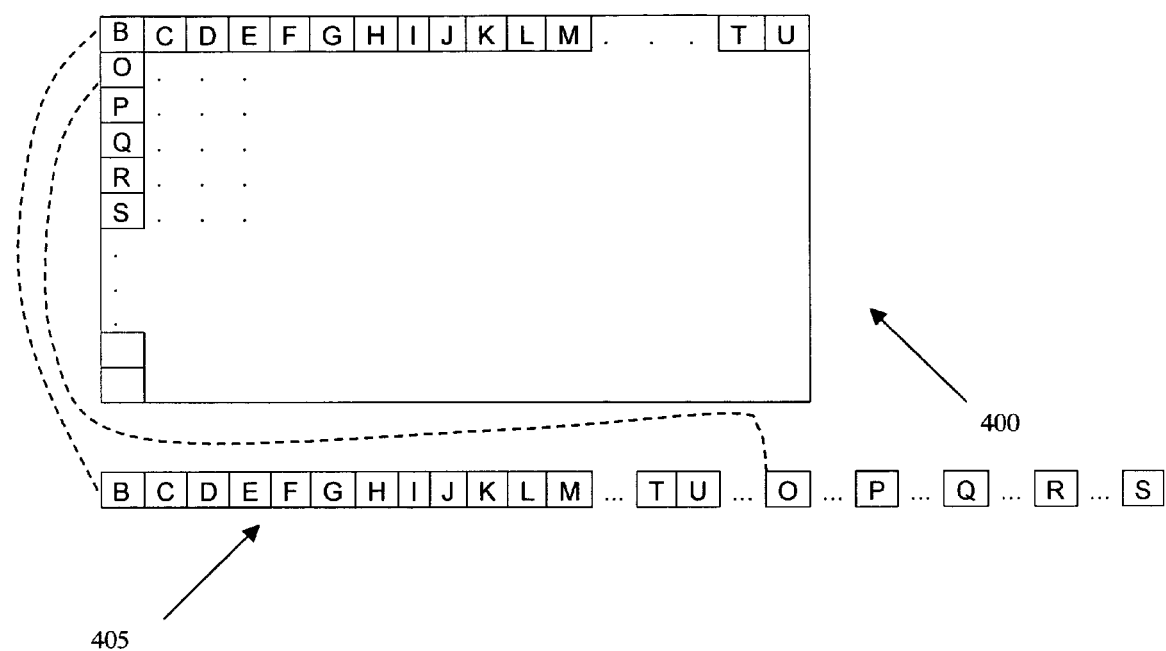
FIG. 4B illustrates a representative video image and a corresponding stream of pixels.

FIG. 4A shows a flow chart that illustrates the compression process utilized by the compressor 204 (FIG. 2) when compressing a stream of video data. FIG. 4B illustrates a representative video image 400 and a corresponding stream of pixel data 405 representing the video image 400. The pixel data is transmitted in an order representing pixels from left to right on each horizontal line, successively, from top to bottom of the video image. As an example, pixels "C" and "D" are considered consecutive pixels within the stream of pixels 405.

This compression process begins at the start step 402, clearing the buffer 222 (FIG. 2) and resetting the repeat counter value to zero. At the step 404, an illumination intensity value representing a current pixel is received. Next, at the step 406, a current line number from the lookup table 310 (FIG. 3A) is obtained for the pixel data corresponding to the current illumination intensity value for the pixel. At the step 408, it is determined whether the current line number for the pixel data is the same as the previous line number. The previous line number is preferably stored in the buffer 222 (FIG. 2). If the previous line number is not stored in the buffer 222 (FIG. 2), then the current line number and the previous line number cannot be the same. If the line number is the same as the previous line number, the repeat counter value is incremented by one, at the step 410. It is then determined whether the repeat counter value is equal to a value of 127, at the step 412. If the repeat counter value is equal to a value of 127, then, at the step 414, the repeat counter value is transmitted out of the compressor 204 (FIG. 2) and into the buffer 223 (FIG. 2) within a data structure that is similar to the data structure 525 (FIG. 5B). Additionally in the step 414, the repeat counter value is reset to a value of zero after being transmitted in the data structure. If the repeat counter is not equal to the value of 127, the process then proceeds directly to the step 416.

Returning back to the step 408, if the current line number is not the same as the previous line number, then it is determined whether the repeat counter value is equal to a value of zero, in the step 420. If it is determined at the step 420, that the repeat counter value is not equal to the value of zero, then at the step 422, the repeat counter value is transmitted out of the compressor 204 (FIG. 2) and into the buffer 223 (FIG. 2) within a data structure that is similar to the data structure 525 (FIG. 5B). Additionally, at the step 422, the repeat counter value is reset to a value of zero after being transmitted in the data structure. If it is determined at the step 420, that the repeat counter value is equal to the value of zero, or after the step 422 is completed, then the line number representing the current illumination intensity value is transmitted out of the compressor 204 (FIG. 2) and into the buffer 223 (FIG. 2), at the step 424, within a data structure that is similar to the data structure 550 (FIG. 5C). Additionally, after the current line number is transmitted, the current line number is stored in the buffer 222 (FIG. 2) as the previous line number, at the step 424. After the step 424 is completed, the process proceeds to the step 416.

At the step 416, it is determined whether there is any additional pixel data corresponding to additional pixels. If there is additional pixel data, then the compression process loops back to the step 404 to receive and process the data representing the next pixel. If there is no additional pixel data, then the process proceeds to the step 418. At the step 418, it is determined whether the repeat counter value is equal to a value of zero.

If the repeat counter value is equal to the value of zero, then the process proceeds to the ending step 428. If the repeat counter value is not equal to the value of zero, then, at the step 426, the repeat counter value is transmitted out of the compressor 204 (FIG. 2) and into the buffer 223 (FIG. 2) within a data structure that is similar to the data structure 525 (FIG. 5B). Additionally in the step 426, the repeat counter value is reset to a value of zero after being transmitted in the data structure. After the step 426, then the process proceeds to the ending step 428.

Figure 6:
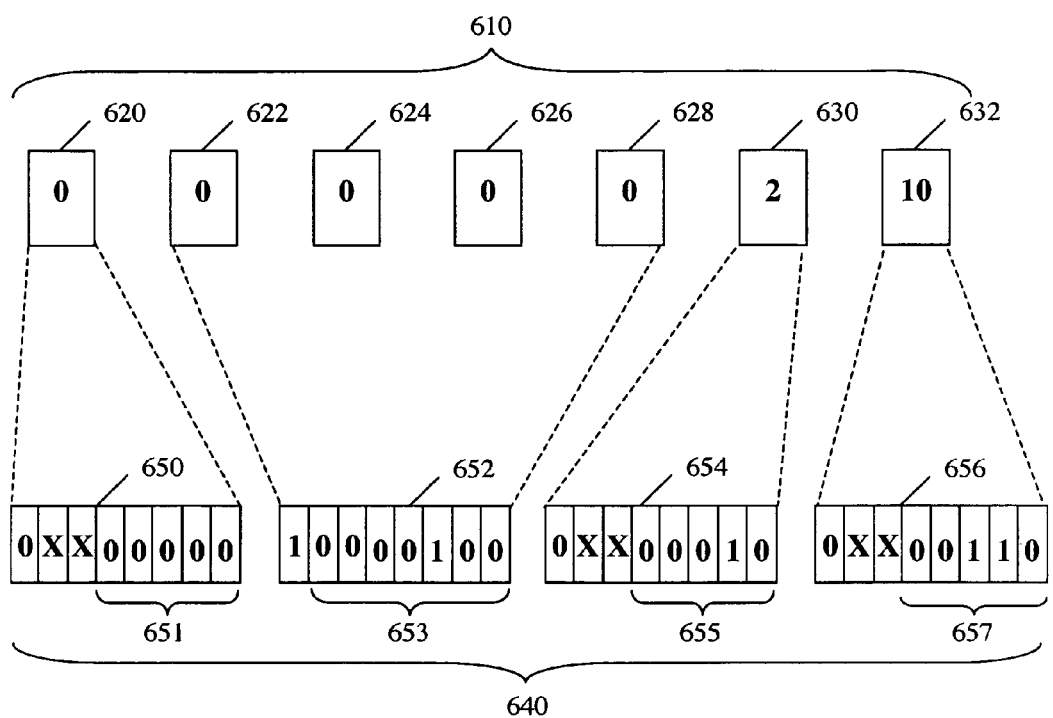
FIG. 6 illustrates a sample data stream representing video pixels and a corresponding compressed data stream.

FIG. 6 illustrates a sample uncompressed illumination intensity data stream 610 including data blocks 620, 622, 624, 626, 628, 630, and 632. Each block includes pixel data representing an illumination intensity value of a corresponding pixel in this uncompressed data stream 610. Preferably, this illumination intensity level is the blue scale value for the particular represented pixel. For example, after the step 406 (FIG. 4A) of obtaining a line number value for each of the data blocks, the blocks 620-628 have a line number value of zero; the block 630 has a line number value of two; and the block 632 has a line number value of ten. A compressed illumination intensity data stream 640 includes data structures 650, 652, 654, and 656. The compressed data stream 640 represents the uncompressed data stream 610 with four data structures. Similar to the illumination intensity data structure 550 (FIG. 5C), the data structures 650, 654, and 656 represent the illumination intensity value of the pixels associated with the data blocks 620, 630, and 632, respectively. A segment 651 of the data structure 650 contains a five bit line number having a value of zero. Similarly, the segments 655 and 657 contain five bit line numbers having values of two and ten, respectively. Similar to the repeat data structure 525 (FIG. 5B), the data structure 652 represents the illumination intensities of the pixels associated with the data blocks 622, 624, 626, and 628. A segment 653 stores the seven bit repeat counter value of four which is the number of times the line number of the prior pixel 620 is repeated. These values are merely exemplary and could be any value. For example, blocks 620-628 could have contained the pixel value of 231 instead of zero and the only difference would be that segment 651 would be have the line number corresponding to 231, e.g. line number 28.

FIG. 7 illustrates software code utilized to decompress a compressed stream of data. This software code includes a decompression lookup table 700, which is utilized within the decompressor 218 (FIG. 2). The decompression lookup table 700 is indexed to provide an output average illumination intensity value corresponding to the received line number from the compression lookup table 310. This decompression lookup table 700 transforms the line number representing the illumination intensity for the stream of pixels which was previously processed by the compressor 204 (FIG. 2) back into a converted illumination intensity data stream having thirty-two levels of illumination intensity.

Similar to the compression lookup table 310 (FIG. 3A), the decompression lookup table 700 utilizes thirty-two levels wherein each level represents the particular line number. For each received line number, the decompression lookup table 700 provides an output average illumination intensity value for a red scale illumination intensity value 710, a green scale illumination intensity value 720, and a blue scale illumination intensity value 730.

Preferably, these output average illumination intensity values are all equal, thereby providing a gray scale image.

Figure 9:
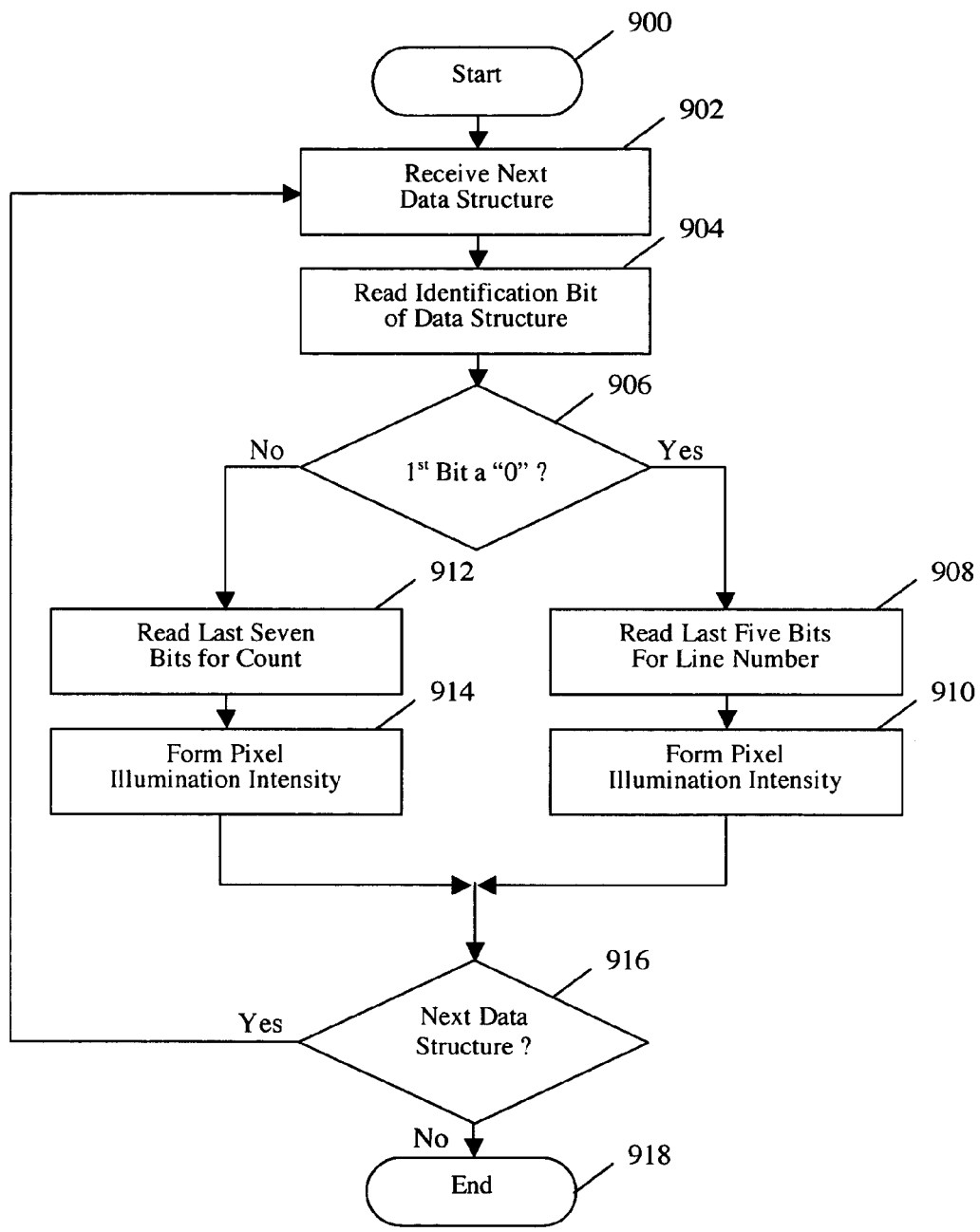
FIG. 9 illustrates a flow chart showing the steps involved during the decompression process of the present invention.

FIG. 9 illustrates a flow chart that shows the preferred decompression process utilized by the decompressor 218 (FIG. 2) to decompress a compressed stream of data.

This decompression process begins at a start step 900 and proceeds to the step 902. At the step 902, a stream of compressed data that was compressed by the compressor 204 (FIG. 2) and includes data representing the illumination intensity of a plurality of pixels waits to be received. The stream of compressed data contains a plurality of data structures that resemble the data structure 500 (FIG. 5A). At the step 902, the next data structure in the stream of compressed data is received as a present data structure. Next, at the step 904, the identification bit within the present data structure received by the step 902 is detected. At the step 906, it is determined if the identification bit which was detected at the step 904 has a value of logical zero or logical one. If the identification bit has a value of logical one, then the present data structure contains a repeat counter value and is decoded at the step 912. If the identification bit has a value of logical zero, then the present data structure contains a line number and is decoded at the step 908.

At the step 912, the repeat counter value is read from the present data structure.

Recall that the repeat counter value stores the number of times to repeat the line number associated with the illumination intensity values of the prior pixel. Next, at the step 914, a particular number of pixels corresponding to a number stored as the repeat counter value, is generated with the illumination intensity values of the prior pixel. The illumination intensity value of the prior pixel is stored in the buffer 221 (FIG. 2) within the decompressor 218 (FIG. 2). For example, if the repeat counter value is five, then five pixels are generated with the illumination intensity values of the prior pixel at the step 914.

At the step 908, the line number is read from the present data structure. The line number corresponds to a row within the decompression lookup table 700 (FIG. 7) that includes the illumination intensity values for the pixel. Next, at the step 910, a pixel is generated having illumination intensity values which correspond to the line number read from the step 908. Additionally, the illumination intensity values are also stored in the buffer 221 (FIG. 2) within the decompressor 218 (FIG. 2). For example, if the line number within the present data structure has a value of two, then according to the decompression lookup table 700 (FIG. 7), the illumination intensity values for the red, green, and blue values of the pixel are sixteen.

After the illumination intensity values are determined at the step 910 or the step 914, it is determined, at the step 916, if there are additional data structures within the compressed stream of data currently being received. If there are additional data structures, then this process loops back to the step 902 where the next data structure is received, and the process begins again. If there are not additional data structures, then this process ends at the step 918.

The compression process as described above and illustrated in the flow chart shown in FIG. 4A is embodied and executed within the compressor 204 (FIG. 2) utilizing the compression lookup table 310 (FIG. 3A). An uncompressed stream of data containing a plurality of eight bit illumination intensity values for a stream of pixels, each having 256 possible levels, is processed within the compressor 204 (FIG. 2). Each illumination intensity value in the uncompressed stream of data is transformed by the compressor 204 (FIG. 2) into a five bit line number having 32 possible levels. This line number represents the illumination intensity value having one of 32 possible levels for a corresponding pixel. In other words, each of the 32 line numbers represents a specific range of illumination intensity values.

By transforming the uncompressed eight bit illumination intensity value having 256 possible levels into the compressed five bit line number having 32 possible levels, some accuracy is lost in this transformation. However, because of inherent characteristics of the source image or of the human eye, this accuracy loss may not be noticeable when viewing a resulting image composed of pixels having illumination intensity values represented by corresponding line numbers.

In order to achieve additional compression, the compressor 204 (FIG. 2) also stores the number of consecutive times a prior line number is repeated as a repeat counter. The compressor 204 (FIG. 2) then replaces the repeated line number(s) with a single repeat data structure that contains the repeat counter. The compressor 204 (FIG. 2) produces a compressed stream of data including line number data structures and repeat data structures, as appropriate.

The decompression process as described in detail above and illustrated in the flow chart shown in FIG. 9 is embodied and executed within the decompressor 218 (FIG. 2) that utilizes the decompression lookup table 700 (FIG. 7). The compressed stream of data is processed by the decompressor 218 (FIG. 2) to transform a combination of line numbers and repeat values into a decompressed stream of illumination intensity values corresponding to the original stream of pixels. When the decompressor 218 (FIG. 2) receives a particular line number, the line number is converted into appropriate illumination intensity values for the corresponding pixel in terms of the red scale, green scale, and blue scale through the decompression lookup table 700 (FIG. 7). The appropriate illumination intensity values are placed in the converted stream of illumination intensity values.

When receiving a particular repeat command from the compressed stream of data, the decompressor 218 (FIG. 2) generates an appropriate number of illumination intensity values, representing a number of pixels, in response to the repeat counter, having the same illumination intensity values as the most recent illumination intensity value in the converted stream of illumination intensity values. Each of the appropriate number of illumination intensity values is placed in the converted stream of illumination intensity values. After the decompression process, the converted stream of illumination intensity values include a plurality of illumination intensity values which closely approximate the plurality of illumination intensity values within the uncompressed stream of data.

Figure 10:
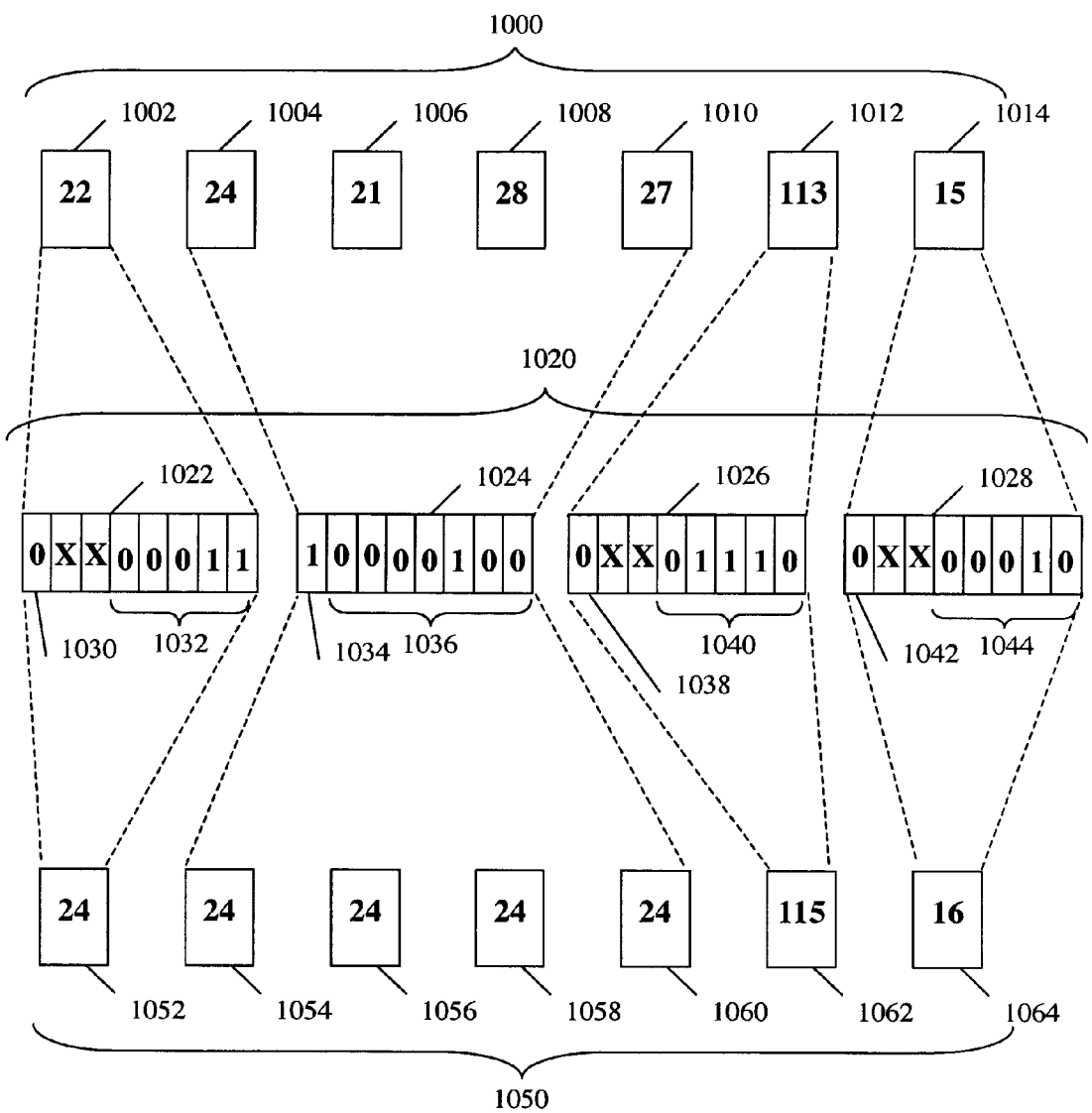
FIG. 10 illustrates an uncompressed data stream, a corresponding compressed data stream, and a corresponding converted data stream of the present invention.

In FIG. 10, sample data streams illustrating the compression and the decompression process of the present invention are shown. The sample data streams include an uncompressed data stream 1000, a compressed data stream 1020, and a decompressed data stream 1050. The uncompressed data stream 1000 includes seven pixel data blocks 1002 through 1014 wherein each of these pixel data blocks represents the illumination intensity value of the particular pixel. The compressed data stream 1020 includes four data blocks 1022-1028 that are generated by the compressor 204 (FIG. 2) and represent the uncompressed data stream 1000. The decompressed data stream 1050 is generated from the decompressor 218 (FIG. 2) and includes seven pixel data blocks 1052-1064 each representing the average illumination intensity value of the particular pixel.

In operation, the compressor 204 (FIG. 2) receives the uncompressed data stream 1000. The pixel data blocks 1002, 1004, 1006, 1008, 1010, 1012, and 1014 store the illumination intensity values "22", "24", "21", "28", "27", "113", and "15", respectively.

According to the step 404 (FIG. 4A), the pixel data block 1002 is received. Next in the step 406 (FIG. 4A), the current line number for the pixel data block 1002 has a value of three, corresponding to the value stored within the storage location in the lookup table 310, representing the illumination intensity value "22." Since the pixel data block 1002 is the first pixel data block within the uncompressed data stream 1000, the current line number is not the same as the previous line number, and the repeat counter value is equal to a value of zero. Accordingly, in the step 424 (FIG. 4A), the current line number having the value of three is transmitted into the buffer 223 (FIG. 2) and is represented as a data structure 1022 in the compressed data stream 1020, which is similar to the data structure 550 (FIG. 5C). Further, the current line number is stored as the previous line number in the buffer 222 (FIG. 2). Next, since the pixel data blocks 1004 through 1014 remain waiting to be processed, the process loops back to the step 404 (FIG. 4A).

In the step 404 (FIG. 4A), the pixel data block 1004 is received. Next in the step 406 (FIG. 4A), the current line number for the pixel data block 1004 has the value of three, corresponding to the value stored within the storage location in the lookup table 310, representing the illumination intensity value "24." In the step 408 (FIG. 4A), the current line number value is determined to be the same as the previous line number value.

Next, the repeat counter value is increased from zero to one, at the step 410 (FIG. 4A).

Since the repeat counter value is not equal to 127, the process proceeds to the step 416 (FIG. 4A). Next, since the pixel data blocks 1006 through 1014 remain waiting to be processed, the process loops back to the step 404 (FIG. 4A).

In the step 404 (FIG. 4A), the pixel data block 1006 is received. Next in the step 406 (FIG. 4A), the current line number for the pixel data block 1006 has the value of three, corresponding to the value stored within the storage location in the lookup table 310, representing the illumination intensity value "21." In the step 408 (FIG. 4A), the current line number value is determined to be the same as the previous line number value.

Next, the repeat counter value is increased from one to two, at the step 410 (FIG. 4A).

Since the repeat counter value is not equal to 127, the process proceeds to the step 416 (FIG. 4A). Next, since the pixel data blocks 1008 through 1014 remain waiting to be processed, the process loops back to the step 404 (FIG. 4A).

In the step 404 (FIG. 4A), the pixel data block 1008 is received. Next in the step 406 (FIG. 4A), the current line number for the pixel data block 1008 has the value of three, corresponding to the value stored within the storage location in the lookup table 310, representing the illumination intensity value "28." In the step 408 (FIG. 4A), the current line number value is determined to be the same as the previous line number value.

Next, the repeat counter value is increased from two to three, at the step 410 (FIG. 4A).

Since the repeat counter value is not equal to 127, the process proceeds to the step 416 (FIG. 4A). Next, since the pixel data blocks 1010 through 1014 remain waiting to be processed, the process loops back to the step 404 (FIG. 4A).

In the step 404 (FIG. 4A), the pixel data block 1010 is received. Next in the step 406 (FIG. 4A), the current line number for the pixel data block 1010 has the value of three, corresponding to the value stored within the storage location in the lookup table 310, representing the illumination intensity value "27." In the step 408 (FIG. 4A), the current line number value is determined to be the same as the previous line number value.

Next, the repeat counter value is increased from three to four, at the step 410 (FIG. 4A).

Since the repeat counter value is not equal to 127, the process proceeds to the step 416 (FIG. 4A). Next, since the pixel data blocks 1012 through 1014 remain waiting to be processed, the process loops back to the step 404 (FIG. 4A).

In the step 404 (FIG. 4A), the pixel data block 1012 is received. Next in the step 406 (FIG. 4A), the current line number for the pixel data block 1012 has a value of fourteen, corresponding to the value stored within the storage location in the lookup table 310, representing the illumination intensity value "113." In the step 408 (FIG. 4A), it is determined that the current line number value is not equal to the previous line number value. Accordingly, the process proceeds to the step 420 (FIG. 4A). In the step 420 (FIG. 4A), it is determined that the repeat counter value is not equal to zero.

Accordingly, in the step 422 (FIG. 4A), the repeat counter value of four is transmitted into the buffer 223 (FIG. 2) and is represented as a data structure 1024 in the compressed data stream 1020 which is similar to the data structure 525 (FIG. 5B). Next in the step 424 (FIG. 4A), the current line number having the value of fourteen is transmitted into the buffer 223 (FIG. 2) and is represented as a data structure 1026 in the compressed data stream 1020 which is similar to the data structure 550 (FIG. 5C).

Further, the current line number is stored as the previous line number in the buffer 222 (FIG. 2). Further, the repeat counter value is reset back to the value of zero. Next, since the pixel data block 1014 remains waiting to be processed, the process loops back to the step 404.

In the step 404 (FIG. 4A), the pixel data block 1014 is received. Next in the step 406 (FIG. 4A), the current line number for the pixel data block 1014 has a value of two, corresponding to the value stored within the storage location in the lookup table 310, representing the illumination intensity value "15." In the step 408 (FIG. 4A), it is determined that the current line number value is not equal to the previous line number value. Accordingly, the process proceeds to the step 420 (FIG. 4A). In the step 420 (FIG. 4A), it is determined that the repeat counter value is equal to zero. Accordingly, in the step 424 (FIG. 4A), the current line number having the value of two is transmitted into the buffer 223 (FIG. 2) and is represented as a data structure 1028 in the compressed data stream 1020, which is similar to the data structure 550 (FIG. 5C).

Further, the current line number is stored as the previous line number in the buffer 222 (FIG. 2). Since there are no more additional pixel data blocks waiting to be processed, and the repeat counter value is equal to zero, the process ends at the ending step 428 (FIG. 4A).

The uncompressed data stream 1000 has been converted into the compressed data stream 1020. The compressed data stream 1020 includes four bytes of data instead of the seven bytes of data included within the uncompressed data stream 1000.

When the decompressor 218 (FIG. 2) receives the compressed data stream 1020, it then generates the decompressed data stream 1050. In operation, the data structure 1022 is received as described in the step 902 (FIG. 9). Next, the identification bit 1030 is determined to have a value of logical zero, in the steps 904 and 906 (FIG. 9), representing that the data structure 1022 is carrying a line number. In response to this determination, the line number value of three is read from the segment 1032 in the step 908 (FIG. 9). According to the lookup table 700 (FIG. 7), the line number value of three corresponds to an average illumination intensity value of twenty-four. The decompressor 218 (FIG. 2) then generates the block 1052 which is encoded with the average illumination intensity value of twenty four and saves the illumination intensity value of twenty-four in the buffer 221 (FIG. 2), at the step 910 (FIG. 9). Next, it is determined that the data block 1024 is the next data structure in the step 916 (FIG. 9).

Accordingly, the process loops back to the step 902 (FIG. 9).

In the step 902 (FIG. 9), the data structure 1024 is received. The identification bit 1034 is determined to have a value of logical one, in the steps 904 and 906 (FIG. 9), representing that the data structure 1024 is carrying a repeat counter value. In response to this determination, a repeat counter value of four is read from the segment 1036, in the step 912 (FIG. 9). The decompressor 218 (FIG. 2) then reads the average illumination intensity value stored in the buffer 221 (FIG. 2) and generates four blocks 1054, 1056, 1058, and 1060 each having the average illumination intensity values of twenty-four.

Next, it is determined that the data structure 1026 is the next data structure in the step 916 (FIG. 9). Accordingly, the process loops back to the step 902 (FIG. 9).

In the step 902 (FIG. 9), the data structure 1026 is received. The identification bit 1038 is determined to have a value of logical zero, in the steps 904 and 906 (FIG. 9), representing that the data structure 1026 is carrying a line number. In response to this determination, the line number of fourteen is read from the segment 1040, in the step 908 (FIG. 9). According to the lookup table 700 (FIG. 7), the line number value of fourteen corresponds to an average illumination intensity value of "115." The decompressor 218 (FIG. 2) then generates the block 1062 which is encoded with the average illumination intensity value of "115" and saves the illumination intensity value of "115" in the buffer 221 (FIG. 2), at the step 910 (FIG. 9). Next, it is determined that the data block 1028 is the next data structure in the step 916 (FIG. 9). Accordingly, the process loops back to the step 902 (FIG. 9).

In the step 902 (FIG. 9), the data structure 1028 is received. The identification bit 1042 is determined to have a value of logical zero, in the steps 904 and 906 (FIG. 9), representing that the data structure 1028 is carrying a line number. In response to this determination, the line number of two is read from the segment 1044, in the step 908 (FIG. 9). According to the lookup table 700 (FIG. 7), the line number value of two corresponds to an average illumination intensity value of "16." The decompressor 218 (FIG. 2) then generates the block 1064 which is encoded with the illumination intensity value of sixteen and saves the illumination intensity value of sixteen in the buffer 221 (FIG. 2), at the step 910 (FIG. 9). Next, in the step 916 (FIG. 9), it is determined that there is no additional data structure. Accordingly, the process ends at the ending step 918 (FIG. 9).

In the preferred embodiment, only the blue scale illumination intensity relating to each pixel is compressed, transmitted, and finally decompressed. Because the preferred embodiment utilizes black and white video images, the decoding table 700 decodes the average illumination value for the blue scale and automatically sets the same illumination intensity for both the red and green scales.

The above example of the preferred embodiment merely illustrates a sample operation of the present invention utilizing black and white video images. It is well within the scope of the present invention to utilize color video images.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

We claim

1. An apparatus comprising:
   a video image capture device configured to capture and output a stream of video images from a video signal;
   a video server coupled with the video image capture device, and configured to process the video images;
   a plurality of sockets coupled with the video server, and configured to respectively transmit the video images to a plurality of receivers in real time; and
   a video controller coupled with the video image capture device, the video server, and the plurality of sockets, and configured to receive from the plurality of receivers, one or more adjustments to one or more operational settings of the video image capture device, the video server, or the sockets, and control operations of the video image capture device, the video server, or the sockets, based at least in part on the received one or more adjustments, to enable respective customization to the real time transmission of the video images to the plurality of receivers.

2. The apparatus of claim 1, wherein the one or more operational settings of the video image capture device include a capture frame rate setting, a capture width setting, a capture height setting, a brightness setting, or a contrast setting, and the video controller is configured to receive from the plurality of receivers, one or more adjustments to the capture frame rate setting, the capture width setting, the capture height setting, the brightness setting, or the contrast setting, and control operations of the video image capture device, based at least in part on the received one or more adjustments to the capture frame rate setting, the capture width setting, the capture height setting, the brightness setting, or the contrast setting.

3. The apparatus of claim 1, wherein the server includes a compressor configured to compress the video images, wherein the video controller is configured to further receive from the plurality of receivers, one or more adjustments to one or more operational settings of the compressor, and further control operations of the compressor, based at least in part on the received one or more adjustments to the one or more operational settings of the compressor.

4. The apparatus of claim 3, wherein the one or more operational settings of the compressor include a compression algorithm setting, a compression image width setting or a compression image height setting, and the video controller is configured to further receive from the plurality of receivers, one or more adjustments to the compression algorithm setting, the compression image width setting or the compression image height setting, and further control operations of the compressor, based at least in part on the received one or more adjustments to the compression algorithm setting, the compression image width setting or the compression image height setting.

5. The apparatus of claim 1, wherein the one or more operational settings of the sockets include a transmission frame rate setting, a transmission width setting, a transmission height setting, or a transmission area setting, and the video controller is configured to receive from the plurality of receivers, one or more adjustments to the transmission frame rate setting, the transmission width setting, the transmission height setting, or the transmission area setting, and control operations of the sockets, based at least in part on the received one or more adjustments to the transmission frame rate setting, the transmission width setting, the transmission height setting, or the transmission area setting.

6. The apparatus of claim 1, further comprising a video recorder coupled with the video server, and configured to record and store the video images, and a recorded video transmitter coupled with the video recorder, and configured to respectively transmit the recorded video images to the plurality of receivers post recording;
wherein the video controller is further coupled with the video recorder and the recorded video transmitter, and configured to further receive from the plurality of receivers, one or more adjustments to one or more operational settings of the video recorder or the recorded video transmitter, and control operations of the video recorder or the recorded video transmitter, based at least in part on the received one or more adjustments to the one or more operational settings of the video recorder or the recorded video transmitter.

7. The apparatus of claim 6, wherein the one or more operational settings of the video recorder and the recorded video transmitter include a start recording setting, a stop recording setting or a transmit recorded video setting, and the video controller is configured to further receive from the plurality of receivers, one or more adjustments to the start recording setting, the stop recording setting or the transmit recorded video setting, based at least in part on the received one or more adjustments to the start recording setting, the stop recording setting or the transmit recorded video setting.

8. The apparatus of claim 1, wherein the video images have associated transmission deadlines, and the video controller is configured to control the sockets to transmit the video images by the respective deadlines, or drop the video images not able to be transmitted by the associated transmission deadlines, and transmit dropped frame indicators in lieu of the dropped video images instead.

9. The apparatus of claim 1, wherein the apparatus is a transmitter to be coupled with a video source device to form a video system, with the video source device configured to provide the transmitter with the video signal.

10. The apparatus of claim 9, wherein the video source is a medical test device including a selected one of an ultrasound device, a sonogram device, an echocardio gram device or an angioplastigram device.

11. The apparatus of claim 1 further comprising a video source coupled with the video capture device, and configured to provide the video capture device with the video signal.

12. The apparatus of claim 11, wherein the video source is a medical test device including a selected one of an ultrasound device, a sonogram device, an echocardio gram device or an angioplastigram device.

13. A method comprising:
capturing and outputting a stream of video images from a video signal;
processing the video images;
respectively transmitting the video images to a plurality of receivers in real time;
receiving from the plurality of receivers, one or more adjustments to one or more operational settings associated with said capturing, processing or transmitting; and
controlling said capturing, processing or transmitting, based at least in part on the received one or more adjustments, to enable respective customization to the real time transmission of the video images to the plurality of receivers.

14. The method of claim 13, wherein the one or more operational settings associated with said capturing include a capture frame rate setting, a capture width setting, a capture height setting, a brightness setting, or a contrast setting, wherein receiving comprises receiving from the plurality of receivers, one or more adjustments to the capture frame rate setting, the capture width setting, the capture height setting, the brightness setting, or the contrast setting, and wherein controlling comprises controlling said capturing based at least in part on the received one or more adjustments to the capture frame rate setting, the capture width setting, the capture height setting, the brightness setting, or the contrast setting.

15. The method of claim 13, wherein processing comprises compressing the video images, wherein receiving comprises receiving from the plurality of receivers, one or more adjustments to one or more operational settings associated with said compressing, and wherein controlling comprises controlling said compressing, based at least in part on the received one or more adjustments to the one or more operational settings associated with said compressing.

16. The method of claim 15, wherein the one or more operational settings associated with said compressing include a compression algorithm setting, a compression image width setting or a compression image height setting, wherein receiving further comprises receiving from the plurality of receivers, one or more adjustments to the compression algorithm setting, the compression image width setting or the compression image height setting, and wherein controlling further controlling said compressing, based at least in part on the received one or more adjustments to the compression algorithm setting, the compression image width setting or the compression image height setting.

17. The method of claim 13, wherein the one or more operational settings associated with transmitting include a transmission frame rate setting, a transmission width setting, a transmission height setting, or a transmission area setting, wherein receiving comprises receiving from the plurality of receivers, one or more adjustments to the transmission frame rate setting, the transmission width setting, the transmission height setting, or the transmission area setting, and controlling comprises controlling said transmitting, based at least in part on the received one or more adjustments to the transmission frame rate setting, the transmission width setting, the transmission height setting, or the transmission area setting.

18. The method of claim 13, further comprising recording and storing the video images, and respectively transmitting the recorded video images to the plurality of receivers post recording;
wherein controlling further comprises controlling said recording and storing, and said transmitting of the recorded video images, wherein receiving further comprises receiving from the plurality of receivers, one or more adjustments to one or more operational settings associated with said recording and storing, or transmitting of recorded video images, and wherein controlling comprises controlling said recording and storing or said transmitting of recorded video images, based at least in part on the received one or more adjustments to the one or more operational settings associated with said recording and transmitting of recorded video images.

19. The method of claim 18, wherein the one or more operational settings associated with recording and storing, and with transmitting of recorded video images, include a start recording setting, a stop recording setting or a transmit recorded video setting, wherein receiving further comprises receiving from the plurality of receivers, one or more adjustments to the start recording setting, the stop recording setting or the transmit recorded video setting, and wherein controlling comprises controlling said recording or transmitting of recorded video images based at least in part on the received one or more adjustments to the start recording setting, the stop recording setting or the transmit recorded video setting.

20. The method of claim 13, wherein the video images have associated transmission deadlines, and controlling comprises controlling transmitting of the video images by the respective deadlines, or dropping the video images not able to be transmitted by the associated transmission deadlines, and transmitting dropped frame indicators in lieu of the dropped video images instead.

21. An article of manufacture comprises computer-readable storage medium, and a plurality of programming instructions configured to enable an apparatus, in response to execution of the programming instructions to perform a number of operations, including:
capturing and outputting a stream of video images from a video signal;
processing the video images;
respectively transmitting the video images to a plurality of receivers in real time;
receiving from the plurality of receivers, one or more adjustments to one or more operational settings associated with said capturing, processing or transmitting; and
controlling said capturing, processing or transmitting, based at least in part on the received one or more adjustments, to enable respective customization to the real time transmission of the video images to the plurality of receivers.

22. The method of claim 21, wherein the operations further comprises recording and storing the video images, and respectively transmitting the recorded video images to the plurality of receivers post recording, wherein controlling further comprises controlling said recording and storing, and said transmitting of the recorded video images, wherein receiving further comprises receiving from the plurality of receivers, one or more adjustments to one or more operational settings associated with said recording and storing, or transmitting of recorded video images, and wherein controlling comprises controlling said recording and storing or said transmitting of recorded video images, based at least in part on the received one or more adjustments to the one or more operational settings associated with said recording and transmitting of recorded video images.

* * * * *

UNITED STATES PATENT AND TRADEMARK OFFICE
CERTIFICATE OF CORRECTION

PATENT NO. : 8,004,572 B2
APPLICATION NO. : 11/633967
DATED : August 23, 2011
INVENTOR(S) : Figueredo et al.

It is certified that error appears in the above-identified patent and that said Letters Patent is hereby corrected as shown below:

Column 22, line 25, in Claim 22, delete "The method of claim 21," and insert -- The article of manufacture of claim 21, --.

Signed and Sealed this
Eighth Day of May, 2012

David J. Kappos
*Director of the United States Patent and Trademark Office*